United States Patent
Bolli et al.

(10) Patent No.: US 7,605,269 B2
(45) Date of Patent: Oct. 20, 2009

(54) THIOPHENE DERIVATIVES AS SPHINGOSINE-1-PHOSPHATE-1 RECEPTOR AGONISTS

(75) Inventors: Martin Bolli, Allschwil (CH); David Lehmann, Basel (CH); Boris Mathys, Egerkingen (CH); Claus Mueller, Weil am Rhein (DE); Oliver Nayler, Arlesheim (CH); Jörg Velker, Huningue (FR); Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 202 days.

(21) Appl. No.: 11/909,436

(22) PCT Filed: Mar. 20, 2006

(86) PCT No.: PCT/IB2006/050850

§ 371 (c)(1),
(2), (4) Date: Sep. 21, 2007

(87) PCT Pub. No.: WO2006/100633

PCT Pub. Date: Sep. 28, 2006

(65) Prior Publication Data

US 2008/0318955 A1    Dec. 25, 2008

(30) Foreign Application Priority Data

Mar. 23, 2005   (WO) ................ PCT/EP2005/003070

(51) Int. Cl.
    *A61K 31/5377*   (2006.01)
(52) U.S. Cl. .......................... 548/131; 549/60; 514/365
(58) Field of Classification Search .............. 548/131; 549/60
    See application file for complete search history.

(56) References Cited

U.S. PATENT DOCUMENTS

| 6,156,787 | A * | 12/2000 | Broughton et al. ......... 514/443 |
| 2008/0176926 | A1 | 7/2008 | Bolli |
| 2008/0194670 | A1 | 8/2008 | Bolli |
| 2008/0257352 | A1 | 10/2008 | Penton |
| 2008/0300294 | A1 | 12/2008 | Bolli |
| 2008/0318955 | A1 | 12/2008 | Bolli |
| 2009/0005421 | A1 | 1/2009 | Bolli |

FOREIGN PATENT DOCUMENTS

| WO | WO-91/15583 A1 | 10/1991 |
| WO | WO 99/46277 A1 | 9/1999 |
| WO | WO 2003/062248 | 7/2003 |
| WO | WO-03/105771 | 12/2003 |
| WO | WO 2003/105771 * | 12/2003 |
| WO | WO-2004/035538 | 4/2004 |
| WO | WO 2004/103279 * | 12/2004 |
| WO | WO-2004/103279 | 12/2004 |
| WO | WO-2006/010379 A1 | 2/2006 |
| WO | WO 2006/010544 | 2/2006 |

OTHER PUBLICATIONS

Dubus et al. (Ann. Chim., 1975, vol. 10; p. 331-336.*
T. Hla, et al., T.J. "An Abundant Transcript Induced in Differentiating Human Endothelial Cells Encodes a Polypeptide with Structural Similiarities to G-protein-coupled Receptors," Biol Chem, 265 (1990), pp. 9308-9313.
Philip L. Gould, "Salt selection for basic drugs," Int. J. Pharm., (1986), 33, pp. 201-217.
A.R. Gangloff, et al., "Synthesis of 3,5-disubstituted-1,2,4-oxadiazoles using tetrabutylammonium fluoride as a mild and efficient catalyst," Tetrahedron Lett, 42 (2001), pp. 1441-1443.
T. Suzuki, et al., "Synthesis of the Selective 5-Hydroxytryptamine 4 (5-HT)4) Receptor Agonist (+)-(s)-2-Chloro-5-methoxy-4-[2-piperidylmethyl)-1,2,4-oxadiaol-3-yl]aniline" Chem. Pharm. Bull., 47 (1999), pp. 120-122.
R.F. Poulain, et al., "Parallel synthesis of 1,2,4-oxadiazoles from carboxylic acides using an imroved, uronium-based, activation," Tetrahedron Lett., 42 (2001), pp. 1495-1498.
R.M. Srivastava, et al., "Synthesis of 3-aryl-5-[thien-3-YL methtyl]-1.2.4-oxadiazoles," Synthetic Commun. 29 (1999), pp. 1437-1450.
E.O. John, et al., "Reaction of (Difluoroamino) difluoroacetonitrile and (Difluoroamino) difluoroacetamidoxime," Inorganic Chemisry, 27 (1988), pp. 3100-3104.
B. Kaboudin, et al., "One-pot synthesis of 1,2,4-oxadiazoles mediated by microwave irradiation under solvent-free condition," Heterocycles 60 (2003), pp. 2287-2292.
A. Hamze, et al., J. Sythesis of a Various 3-Substitued 1,2,4-Oxadiazole-Contraining Chiral β3- and α-Amino Acids from Fmoc-Protected Aspartic Acid, J. Org. Chem. 68 (2003), pp. 7316-7321.
J. Cui, et al., "Design and Synthesis of Highly Constrained Factor Xa Inhibitors: Amidine-Substituted Bis(benzoyl)-[1,3]-diazepan-2-ones and Bis(benzylidene)-bis (gemdimethyl)cycloketones," Bioorg. Med. Chem. 11 (2003), pp. 3379-3392.
T.W. Greene, et al., "Protective Groups in Organic Synthesis," 3rd Edition, Wiley New York, 1991.
P.J. Kocienski, Protecting Group, Thieme Stuttgart, 1994.
C. D. Bedford et al., "Nonquaternary Cholinesterase Reactivators. 3. (3(5)-Substituted 1,2,4-Oxadiaxo1-5(3)-aldoximes and 1,2,4-Oxadiazole-5(3)-thiocarbohydroximates as Reactivators of Organophosphonate-Inhibited Eel and Human Acetylcholinesterase in Vitro," J. Med. Chem. 29 (1986), pp. 2174-2183.
D. Dubus, et al., "Synthese De Diheterocycles En Serie Oxadiazole-1,2,4," Annales de Chimie (Paris, France) 10 (1975), pp. 331-336.
B. Hedegaard, et al., "Thiophene Chemistry—XIX," Tetrahedron 27 (1971), pp. 3853-3859.

(Continued)

*Primary Examiner*—Kamal A Saeed
*Assistant Examiner*—Valerie Rodriguez-Garcia
(74) *Attorney, Agent, or Firm*—Hoxie & Associates LLC; Brittany La

(57) ABSTRACT

The invention relates to novel thiophene derivatives, their preparation and their use as pharmaceutically active compounds. Said compounds particularly act as immunosuppressive agents.

17 Claims, No Drawings

OTHER PUBLICATIONS

S.A. Popov, et al., "Synthesis of New Chiral Heterocycles of the Pyrazole and 2-Isoxazoline Types from (+)-3-Carene," Tetrahedron: Asymmetry vol. 5, No. 3 (1994), pp. 479-489.

S.A. Popov, et al., "Synthesis of 2-Alkyl and 2-Aryl Pyrimidines from β-Chlorovinyl Ketones of Cyclopentanone Type," Synthetic Commmunications, 31(2), (2001), pp. 233-243.

W. Cocker, et al., "A Convenient Preparation of (−)-β-3,4-Epoxycarane," Tetrahedron Letters No. 51, (1969), pp. 4451-4452.

S. Lochynski, et al., "Modification of Synthesis of Dihydrochrysanthemolactone from (+)-Car-3-ene," Journ f. prakt. Chemie. Band 330, Heft 2, (1988), pp. 284-288.

M. Walkowicz, et al., "Uber Stereoisomere 6,6-Dimethyl-Bicyclo-[3.1.0]-Hexanole-3," Roczniki Chemii Ann. Soc. Chim. Polonorum 41(1967) pp. 927-937.

H. Kuczynski, et al., "0 Krystalicznym (−)-Dwubromo-3,4-Karanie," Roczniki Chemii Ann. Soc. Chim. Polonorum 38, (1964), pp. 1625-1633.

A.V. Pol, et al., "Oxidation of $\Delta^3$-Carene & α-Pinene with Thallium(III) Nitrate," Indian J. Chem., vol. 19B, (1980) pp. 603-604.

B. Xu, et al., "Acyclic Analogues of Adenosine Bisphophates as P2Y Receptor Antagonists: Phosphate Substitution Leads to Multiple Pathways of Inhibition of Platelet Aggregation," J. Med. Chem. 45 (2002), pp. 5694-5709.

V.M. Christi, et al., "Einige Valene von Benzanellierten fuenfgliedrigen Hetroarenen-Synthesen und NMR-Spektren," Angewandte Chemie VCH Verlagsgesellschaft, Weinheim, DE, vol. 102, No. 6 (1990) pp. 704-706.

U.S. Appl. No. 11/993,563, filed Dec. 21, 2008, Actelion Pharmaceuticals Ltd.

U.S. Appl. No. 12/160,520, filed Jul. 10, 2008, Actelion Pharmaceuticals Ltd.

* cited by examiner

THIOPHENE DERIVATIVES AS SPHINGOSINE-1-PHOSPHATE-1 RECEPTOR AGONISTS

CROSS REFERENCE TO RELATED APPLICATIONS

This application is a United States National Stage Application under 35 U.S.C. 371 of PCT Application No. PCT/IB2006/050850, filed on Mar. 20, 2006, which claims the benefit of PCT Application No. PCT/EP2005/003070, filed on Mar. 23, 2005, the contents of each of which are incorporated herein by reference.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunosuppressive effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunosuppressive therapy with a reduced propensity for infections when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO91/15583 published 17 Oct. 1991; WO99/46277 published 16 Sep. 1999. These references are incorporated herewith in their entirety. The potency and efficacy of the compounds of Formula (I) are assessed using a GTPγS assay to determine $EC_{50}$ values and by measuring the circulating lymphocytes in the rat after oral administration, respectively.

The following paragraphs provide definitions of the various chemical moieties that make up the compounds according to the invention and are intended to apply uniformly throughout the specification and claims unless an otherwise expressly set out definition provides a broader definition.

The term lower alkyl, alone or in combination with other groups, means saturated, branched or preferably straight chain groups with one to five carbon atoms, preferably one to three carbon atoms. Examples of lower alkyl groups are methyl, ethyl, n-propyl, iso-propyl, n-butyl, iso-butyl, sec-butyl, tert-butyl, or n-pentyl.

The term lower alkoxy means an R—O group, wherein R is a lower alkyl. Preferred examples of lower alkoxy groups are methoxy, ethoxy, propoxy, iso-propoxy, iso-butoxy, sec-butoxy or tert-butoxy.

The term hydroxy-lower alkoxy means a straight or branched alkoxy chain bearing a hydroxy group whereby there are at least two carbon atoms between the hydroxy group and the oxygen of the lower alkoxy group. Examples of hydroxy-lower alkoxy groups are 2-hydroxy-ethoxy, 3-hydroxy-propoxy, 2-hydroxy-propoxy, 4-hydroxy-butoxy, 3-hydroxy-1-methyl-propoxy, 3-hydroxy-butoxy, etc.

The term mono- or di-lower alkylamino means an R'—NH— or an R'—NR"— group, wherein R' and R" are each independently a lower alkyl group. Preferred examples of mono- or di-lower alkylamino groups are methylamino, ethylamino, N,N-dimethylamino, or N-methyl-N-ethylamino.

The term halogen means fluoro, chloro, bromo or iodo, preferably fluoro or chloro.

Salts are preferably the pharmaceutically acceptable salts of the compounds of Formula (I).

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or poly-acid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanedisulfonic acid, p-toluenesulfonic acid, salicylic acid, succinic acid, trifluoroacetic acid, and the like that are non toxic to living organisms or in case the compound of Formula (I) is acidic in nature with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", Int. J. Pharm. (1986), 33, 201-217.

i) The invention relates to novel thiophene derivatives of the Formula (I),

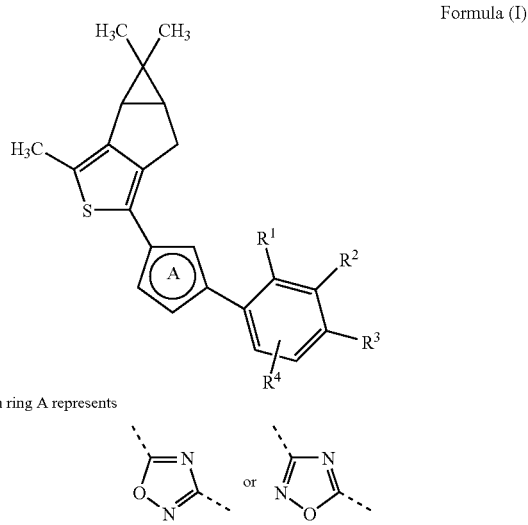

Formula (I)

wherein ring A represents $R^1$ represents hydrogen, lower alkyl, lower alkoxy, or halogen;

$R^2$ represents hydrogen, lower alkyl, lower alkoxy, trifluoromethyl, trifluoromethoxy, or halogen;

$R^3$ represents hydrogen, hydroxy-lower alkyl, 2,3-dihydroxypropyl, di-(hydroxy-lower alkyl)-lower alkyl, —CH$_2$—(CH$_2$)$_k$—NR$^{31}$R$^{32}$, (azetidine-3-carboxylic acid)-1-yl-methyl, (azetidine-3-carboxylic acid lower alkylester)-1-yl-methyl, 2-[(azetidine-3-carboxylic acid)-1-yl]-ethyl, 2-[(azetidine-3-carboxylic acid lower alkylester)-1-yl]-ethyl, 3-[(azetidine-3-carboxylic acid)-1-yl]-propyl, 3-[(azetidine-3-carboxylic acid lower alkylester)-1-yl]-propyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, 2-[(pyrrolidine-3-carboxylic acid)-1-yl]-ethyl, 2-[(pyrrolidine-3-carboxylic acid lower alkylester)-1-yl]-ethyl, 2-[(pyrrolidine-2-carboxylic acid)-1-yl]-ethyl, 2-[(pyrrolidine-2-carboxylic acid lower alkylester)-1-yl]-ethyl, 3-[(pyrrolidine-3-carboxylic acid)-1-yl]-propyl, 3-[(pyrrolidine-3-carboxylic acid lower alkylester)-1-yl]-propyl, 3-[(pyrrolidine-2-carboxylic acid)-1-yl]-propyl, 3-[(pyrrolidine-2-carboxylic acid lower alkylester)-1-yl]-propyl, —CH$_2$—(CH$_2$)$_n$—CONR$^{31}$R$^{32}$, —CO—NHR$^{31}$, —(CH$_2$)$_n$CH(OH)—CH$_2$—NR$^{31}$R$^{32}$, hydroxy, lower alkoxy, fluoro-lower alkoxy, hydroxy-lower alkoxy, di-(hydroxy-lower alkyl)-lower alkoxy, 1-glyceryl, 2-glyceryl, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(lower alkyl)-piperazin-1-yl]-ethoxy, 2-[4-(2-hydroxy-ethyl)-piperazin-1-yl]-ethoxy, 3-piperazin-1-yl-propoxy, 3-[4-(lower alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)-1-yl]-ethoxy, 2-[(2-hydroxy-pyrrolidine)-1-yl]-ethoxy, 2-[(3-hydroxy-pyrrolidine)-1-yl]- ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, 3-carbamoyl-propoxy, 3-(lower alkylcarbamoyl)propoxy, 3-(2-hydroxyethylcarbamoyl)propoxy, —$OCH_2$—CH(OH)—$CH_2$—$NR^{31}R^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(lower alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —$NR^{31}R^{32}$, —NHCO—$R^{31}$, —$CH_2$—$(CH_2)_k$—$NHSO_2R^{33}$, —$(CH_2)_n$CH(OH)—$CH_2$—$NHSO_2R^{33}$, —$OCH_2$—$(CH_2)_m$—$NHSO_2R^{33}$, —$OCH_2$—CH(OH)—$CH_2$—$NHSO_2R^{33}$, —$CH_2$—$(CH_2)_k$—$NHCOR^{34}$, —$(CH_2)_n$CH(OH)—$CH_2$—NH-$COR^{34}$, —$OCH_2$—$(CH_2)_m$—$NHCOR^{34}$, or —$OCH_2$—CH(OH)—$CH_2$—$NHCOR^{34}$;

$R^{31}$ represents hydrogen, methyl, ethyl, 1-propyl, 2-propyl, 2-hydroxyethyl, 2-hydroxy-1-hydroxymethyl-ethyl, 2-lower alkoxyethyl, 3-hydroxypropyl, 3-lower alkoxypropyl, 2-aminoethyl, 2-(lower alkylamino)ethyl, 2-(di-(lower alkyl)amino)ethyl, carboxymethyl, lower alkylcarboxymethyl, 2-carboxyethyl, or 2-(lower alkylcarboxy)ethyl;

$R^{32}$ represents hydrogen, methyl, or ethyl;

$R^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

$R^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

n represents 0, 1, or 2; and $R^4$ represents hydrogen, lower alkyl, or halogen;

and configurational isomers, mixtures of enantiomers such as racemates, diastereomers, mixtures of diastereomers, diastereomeric racemates, and mixtures of diastereomeric racemates, as well as salts, solvent complexes, and morphological forms thereof.

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to configurational isomers, mixtures of enantiomers such as racemates, diastereomers, mixtures of diastereomers, diastereomeric racemates, and mixtures of diastereomeric racemates, as well as salts, solvent complexes, and morphological forms, as appropriate and expedient.

ii) A particular embodiment of the invention relates to thiophene derivatives according to embodiment i), wherein the compounds represented in Formula (I) constitute the (1aR, 5aS)-isomer of the 1,1,2-trimethyl-1,1a,5,5a-tetrahydro-3-thia-cyclopropa[a]pentalene derivative.

iii) A preferred embodiment of the invention relates to thiophene derivatives according to embodiment i), wherein the compounds represented in Formula (I) constitute the (1aS, 5aR)-isomer of the 1,1,2-trimethyl-1,1a,5,5a-tetrahydro-3-thia-cyclopropa[a]pentalene derivative.

iv) A preferred embodiment of the invention relates to thiophene derivatives according to any one of embodiments i) to iii), wherein the compounds represented in Formula (I) constitute a 5-thiophen-2-yl-[1,2,4]oxadiazole derivative.

v) Another preferred embodiment of the invention relates to thiophene derivatives according to any one of embodiments i) to iii), wherein the compounds represented in Formula (I) constitute a 3-thiophen-2-yl-[1,2,4]oxadiazole derivative.

vi) A preferred embodiment of the invention relates to thiophene derivatives according to any one of embodiments i) to v), wherein $R^1$, $R^2$, and $R^4$ represent hydrogen.

vii) Another preferred embodiment of the invention relates to thiophene derivatives according to any one of embodiments i) to v), wherein $R^1$ represents hydrogen and $R^2$ and $R^4$ represent a methyl group.

viii) Another preferred embodiment of the invention relates to thiophene derivatives according to any one of embodiments i) to v), wherein $R^1$ represents hydrogen, $R^2$ represents a methyl group and $R^4$ represents an ethyl group.

ix) Another preferred embodiment of the invention relates to thiophene derivatives according to any one of embodiments i) to v), wherein $R^1$ represents hydrogen, $R^2$ represents a methoxy group and $R^4$ represents chlorine.

x) A further embodiment of the invention relates to thiophene derivatives according to any one of embodiments i) to ix), wherein $R^3$ represents hydrogen, hydroxy-lower alkyl, 2,3-dihydroxypropyl, di-(hydroxy-lower alkyl)-lower alkyl, —$CH_2$—$(CH_2)_k$—$NR^{31}R^{32}$, (azetidine-3-carboxylic acid)-1-yl-methyl, (azetidine-3-carboxylic acid lower alkylester)-1-yl-methyl, 2-[(azetidine-3-carboxylic acid)-1-yl]-ethyl, 2-[(azetidine-3-carboxylic acid lower alkylester)-1-yl]-ethyl, 3-[(azetidine-3-carboxylic acid)-1-yl]-propyl, 3-[(azetidine-3-carboxylic acid lower alkylester)-1-yl]-propyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, 2-[(pyrrolidine-3-carboxylic acid)-1-yl]-ethyl, 2-[(pyrrolidine-3-carboxylic acid lower alkylester)-1-yl]-ethyl, 2-[(pyrrolidine-2-carboxylic acid)-1-yl]-ethyl, 2-[(pyrrolidine-2-carboxylic acid lower alkylester)-1-yl]-ethyl, 3-[(pyrrolidine-3-carboxylic acid)-1-yl]-propyl, 3-[(pyrrolidine-3-carboxylic acid lower alkylester)-1-yl]-propyl, 3-[(pyrrolidine-2-carboxylic acid)-1-yl]-propyl, 3-[(pyrrolidine-2-carboxylic acid lower alkylester)-1-yl]-propyl, —$CH_2$—$(CH_2)_n$—$CONR^{31}R^{32}$, —CO—$NHR^{31}$, —$(CH_2)_n$CH(OH)—$CH_2$—$NR^{31}R^{32}$, hydroxy, lower alkoxy, fluoro-lower alkoxy, hydroxy-lower alkoxy, di-(hydroxy-lower alkyl)-lower alkoxy, 1-glyceryl, 2-glyceryl, 2-hydroxy-3-methoxy-propoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-(lower alkyl)-piperazin-1-yl]-ethoxy, 2-[4-(2-hydroxy-ethyl)-piperazin-1-yl]-ethoxy, 3-piperazin-1-yl-propoxy, 3-[4-(lower alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, 3-carbamoyl-propoxy, 3-(lower alkylcarbamoyl)propoxy, 3-(2-hydroxyethylcarbamoyl)propoxy, —$OCH_2$—CH(OH)—$CH_2$—$NR^{31}R^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(lower alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, or —$NR^{31}R^{32}$, —NHCO—$R^{31}$ and wherein $R^{31}$ and $R^{32}$ are as defined above.

xi) A further preferred embodiment of the invention relates to thiophene derivatives according to any one of embodiments i) to ix), wherein $R^3$ represents hydroxy-lower alkoxy, di-(hydroxy-lower alkyl)-lower alkoxy, 1-glyceryl, 2-glyceryl, 2-hydroxy-3-methoxy-propoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-(lower alkyl)-piperazin-1-yl]-ethoxy, 2-[4-(2-hydroxy-ethyl)-piperazin-1-yl]-ethoxy, 3-piperazin-1-yl-propoxy, 3-[4-(lower alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, 3-carbamoyl-propoxy, 3-(lower alkylcarbamoyl)propoxy, 3-(2-hydroxyethylcarbamoyl)propoxy, —$OCH_2$—CH(OH)—$CH_2$—$NR^{31}R^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(lower alkyl)-piperazin-1-yl]-propoxy, 2-hydroxy-3-[4-(2-hydroxy-ethyl)-piperazin-1-yl]-propoxy, or 2-hydroxy-3-morpholin-4-yl-propoxy and wherein $R^{31}$ and $R^{32}$ are as defined above.

xii) Another further preferred embodiment of the invention relates to thiophene derivatives according to any one of embodiments i) to ix), wherein $R^3$ represents hydroxy-lower alkyl, 2,3-dihydroxypropyl, di-(hydroxy-lower alkyl)-lower alkyl, —$CH_2$—$(CH_2)_k$—$NR^{31}R^{32}$, (azetidine-3-carboxylic acid)-1-yl-methyl, (azetidine-3-carboxylic acid lower alkylester)-1-yl-methyl, 2-[(azetidine-3-carboxylic acid)-1-yl]-ethyl, 2-[(azetidine-3-carboxylic acid lower alkylester)-1-yl]-ethyl, 3-[(azetidine-3-carboxylic acid)-1-yl]-propyl, 3-[(azetidine-3-carboxylic acid lower alkylester)-1-yl]-propyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, 2-[(pyrrolidine-3-carboxylic acid)-1-yl]-ethyl, 2-[(pyrrolidine-3-carboxylic acid lower alkylester)-1-yl]-ethyl, 2-[(pyrrolidine-2-carboxylic acid)-1-yl]-ethyl, 2-[(pyrrolidine-2-carboxylic acid lower alkylester)-1-yl]-ethyl, 3-[(pyrrolidine-3-carboxylic acid)-1-yl]-propyl, 3-[(pyrrolidine-3-carboxylic acid lower alkylester)-1-yl]-propyl, 3-[(pyrrolidine-2-carboxylic acid)-1-yl]-propyl, 3-[(pyrrolidine-2-carboxylic acid lower alkylester)-1-yl]-propyl, —$CH_2$—$(CH_2)_n$—$CONR^{31}R^{32}$, —CO—$NHR^{31}$, or —$(CH_2)_n$CH(OH)—$CH_2$—$NR^{31}R^{32}$ and wherein $R^{31}$ and $R^{32}$ are as defined above.

xiii) Another further preferred embodiment of the invention relates to thiophene derivatives according to any one of embodiments i) to ix), wherein $R^3$ represents di-(hydroxy-lower alkyl)-lower alkoxy, 1-glyceryl, —$OCH_2$—$(CH_2)_m$—$NR^{31}R^{32}$, —O—$CH_2$—$CONR^{31}R^{32}$, or —$OCH_2$—CH(OH)—$CH_2$—$NR^{31}R^{32}$, wherein $R^{31}$ represents methyl or 2-hydroxyethyl and $R^{32}$ represents hydrogen.

xiv) Another very preferred embodiment of the invention relates to thiophene derivatives according to any one of embodiments i) to ix), wherein $R^3$ represents —$CH_2$—$(CH_2)_k$—$NHSO_2R^{33}$, —$(CH_2)_n$CH(OH)—$CH_2$—$NHSO_2R^{33}$, —$OCH_2$—$(CH_2)_m$—$NHSO_2R^{33}$, —$OCH_2$—CH(OH)—$CH_2$—$NHSO_2R^{33}$, —$CH_2$—$(CH_2)_k$—$NHCOR^{34}$, —$(CH_2)_n$CH(OH)—$CH_2$—$NHCOR^{34}$, —$OCH_2$—$(CH_2)_m$—$NHCOR^{34}$, or —$OCH_2$—CH(OH)—$CH_2$—$NHCOR^{34}$ and wherein $R^{33}$ and $R^{34}$ are as defined above.

xv) Specific thiophene derivatives according to Formula (I) are:

4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol, 2-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethanol, 1-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-2-ol, (2S)-3-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propane-1,2-diol, (2R)-3-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propane-1,2-diol, 1-methoxy-3-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-2-ol, 2-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-propane-1,3-diol, 3-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-1-ol, dimethyl-(2-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethyl)-amine, dimethyl-(2-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethyl)-amine, 2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol, 2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethanol, 1-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-2-ol, (2S)-3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propane-1,2-diol, (2R)-3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propane-1,2-diol, 1-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-3-methoxy-propan-2-ol, 2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-propane-1,3-diol, 3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-1-ol, (2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethyl)-dimethyl-amine, 3-[3,5-dimethyl-4-(2-pyrrolidin-1-yl-ethoxy)-phenyl]-5-((1aS,5aR)-1,1,2-trimethyl-1,1a,5,5a-tetrahydro-3-thia-cyclopropa[a]pentalen-4-yl)-[1,2,4]oxadiazole, 4-(2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethyl)-morpholine, 3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propylamine, (3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-methyl-amine, (3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-dimethyl-amine, 2-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propylamino)-ethanol, 3-[3,5-dimethyl-4-(3-pyrrolidin-1-yl-propoxy)-phenyl]-5-((1aS,5aR)-1,1,2-trimethyl-1,1a,5,5a-tetrahydro-3-thia-cyclopropa[a]pentalen-4-yl)-[1,2,4]oxadiazole, (3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-propyl-amine, 2-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propylamino)-propane-1,3-diol, $N_1$-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-ethane-1,2-diamine, 1-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-pyrrolidine-2-carboxylic acid, 1-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-pyrrolidine-3-carboxylic acid, 2-[4-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-piperazin-1-yl]-ethanol, 2-amino-2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-propane-1,3-diol, (3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-isopropyl-amine, (3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-(2-ethoxy-ethyl)-amine, 2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenol, 2-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxy}-ethanol, 1-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxy}-propan-2-ol, 3-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxy}-propane-1,2-diol, 3-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxy}-propane-1,2-diol, 2-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxymethyl}-propane-1,3-diol, and 3-(3-trifluoromethyl-phenyl)-5-((1aS,5aR)-1,1,2-trimethyl-1,1a,5,5a-tetrahydro-3-thia-cyclopropa[a]pentalen-4-yl)-[1,2,4]oxadiazole.

The compounds of Formula (I) and their pharmaceutically acceptable salts can be used as medicaments, e.g. in the form of pharmaceutical compositions for enteral, parental or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, The Science and Practice of Pharmacy, 20th Edition, Philadelphia College of Pharmacy and Science) by bringing the described compounds of Formula (I) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The pharmaceutical compositions comprising a compound of Formula (I) are useful for the prevention and treatment of disorders associated with an activated immune system.

Such diseases or disorders are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Preferably, the diseases or disorders to be prevented or treated with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a patient a pharmaceutically active amount of a compound of Formula (I).

Furthermore, compounds of the Formula (I) are also useful, in combination with one or several immunomodulating agents, for the prevention or treatment of the diseases and disorders mentioned herein. According to a preferred embodiment of the invention, said agent is selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

Still a further object of the present invention is a process to prepare a pharmaceutical composition comprising a compound of the Formula (I) by mixing one or more active ingredients with inert excipients in a manner known per se.

The present invention also relates to the use of a compound of Formula (I) for the preparation of a pharmaceutical composition, optionally for use in combination with one or several immunomodulating agents, for the prevention or treatment of the diseases and disorders mentioned herein.

The present invention also relates to pro-drugs of a compound of Formula (I) that convert in vivo to the compound of Formula (I) as such. Any reference to a compound of Formula (I) is therefore to be understood as referring also to the corresponding pro-drugs of the compound of Formula (I), as appropriate and expedient.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

Compounds of Formula (I), wherein Formula (I) represents a 5-thiophen-2-yl-[1,2,4]oxadiazole derivative, are prepared by reacting a compound of Structure 1 in a solvent such as xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, etc.) (Lit: e.g. A. R. Gangloff, J. Litvak, E. J. Shelton, D. Sperandio, V. R. Wang, K. D. Rice, Tetrahedron Lett. 42 (2001), 1441-1443; T. Suzuki, K. Iwaoka, N. Imanishi, Y. Nagakura, K. Miyta, H. Nakahara, M. Ohta, T. Mase, Chem. Pharm. Bull. 47 (1999), 120-122; R. F. Poulain, A. L. Tartar, B. P. Déprez, Tetrahedron Lett. 42 (2001), 1495-1498; R. M. Srivastava, F. J. S. Oliveira, D. S. Machado, R. M. Souto-Maior, Synthetic Commun. 29 (1999), 1437-1450; E. O. John, J. M. Shreeve, Inorganic Chemistry 27 (1988), 3100-3104; B. Kaboudin, K. Navaee, Heterocycles 60 (2003), 2287-2292).

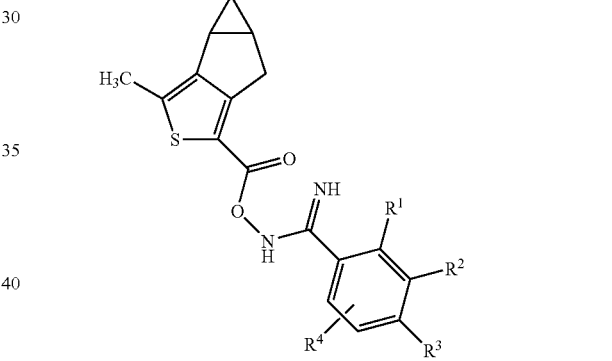

Structure 1

Compounds of Structure 1 may be prepared by reacting a compound of Structure 2 with a compound of Structure 3 in a solvent such as DMF, THF, etc. in the presence or absence of one or more coupling agents such as TBTU, DCC, EDC, HBTU, HOBt, CDI, etc. and in the presence or absence of a base such as triethylamine, Hünig's base, NaH, $K_2CO_3$, etc. (Lit: e.g. A. Hamze, J.-F. Hernandez, P. Fulcrand, J. Martinez, J. Org. Chem. 68 (2003) 7316-7321; and the literature cited above).

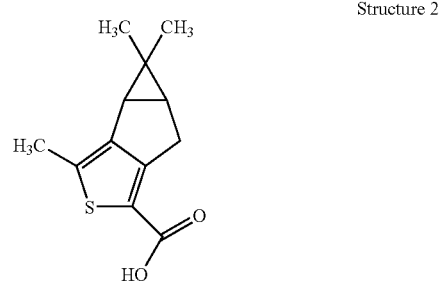

Structure 2

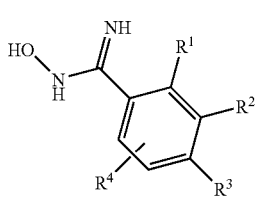

Structure 3

Compounds of Structure 3 may be prepared by reacting a compound of Structure 4 with hydroxylamine or one of its salts in a solvent such as methanol, ethanol, pyridine, etc. in the presence or absence of a base such as Na$_2$CO$_3$, K$_2$CO$_3$, triethylamine, etc. (Lit: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO Patent (Merck & Co., Inc., USA). WO 2004035538; B. Kaboudin, K. Navaee, *Heterocycles* 60 (2003), 2287-2292).

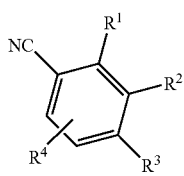

Structure 4

Depending on the nature of the functionalities present in the residues R$^1$ to R$^4$ in Structures 1, 3 or 4, and in Formula (I), these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues R$^1$ to R$^4$, in particular R$^3$, may also be introduced in later steps that follow the cyclisation of a compound of Structure 1 by performing the above reaction sequence with suitable precursors of the compounds of Structures 1, 3 and 4, respectively. The compounds of Structure 4 or their precursors are either commercially available or are prepared according to procedures known to a person skilled in the art.

The compound of Structure 2 may be prepared by reacting a compound of Structure 5 with an aqueous base such as aq. NaOH, aq. LiOH, aq. KOH, etc. or an acid such as aq. HCl, TFA, etc. in a solvent such as water, ethanol, methanol, THF, etc. or mixtures thereof.

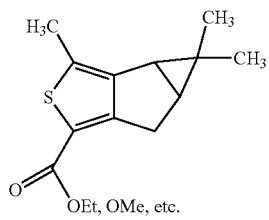

Structure 5

The compounds of Structure 5 are prepared by treating a compound of Structure 6 with a non aqueous base such as NaOMe, NaOEt, KO-tert.-Bu, DBU, etc. in a solvent such as methanol, ethanol, THF, DMF, etc. or mixtures thereof preferably at elevated temperatures.

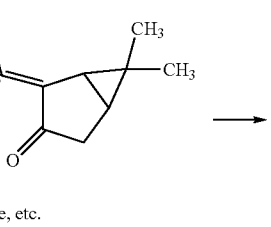

Structure 6

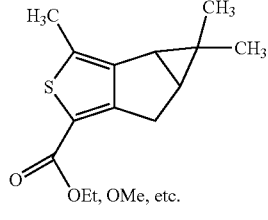

Structure 5

The compounds of Structure 6 are prepared by treating the compound of Structure 7 with a 2-mercaptoacetic acid ester in the presence of a base such a NaH in THF, dioxane, DMF, or mixtures thereof. In addition, the compounds of Structure 2 may also be prepared in a one-pot three step procedure starting from a compound of structure 7 following the above reaction sequence.

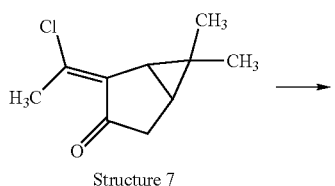

Structure 7

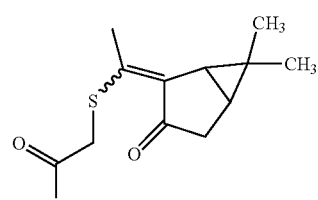

Structure 6

Compounds of Formula (I), wherein Formula (I) represents a 3-thiophen-2-yl-[1,2,4]oxadiazole derivative, are prepared by reacting a compound of Structure 8 in a solvent such as xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, etc.) (Lit. e.g. see above).

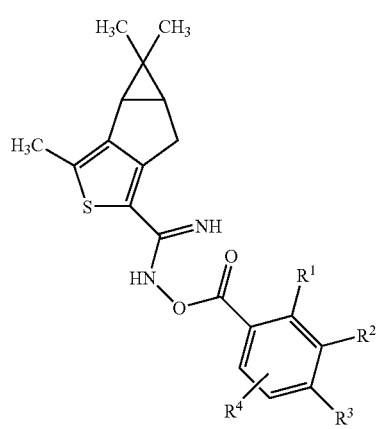

Structure 8

Compounds of Structure 8 may be prepared by reacting a compound of Structure 9 with a compound of Structure 10 in a solvent such as DMF, THF, etc. in the presence or absence of one or more coupling agents such as TBTU, DCC, EDC, HBTU, HOBt, CDI, etc. and in the presence or absence of a base such as triethylamine, Hünig's base, NaH, $K_2CO_3$, etc. (Lit: e.g. see above).

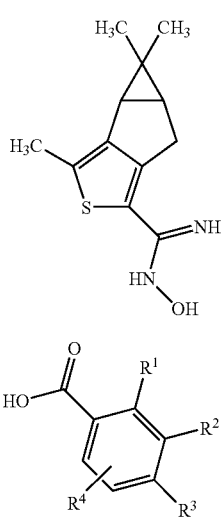

Structure 9

Structure 10

Compounds of Structure 9 may be prepared by reacting a compound of Structure 11 with hydroxylamine or one of its salts in a solvent such as methanol, ethanol, pyridine, etc. in the presence or absence of a base such as $Na_2CO_3$, $K_2CO_3$, triethylamine, etc. (Lit: e.g. C. D. Bedford, R. A. Howd, O. D. Dailey, A. Miller, H. W. Nolen, R. A. Kenley, J. R. Kern, J. S. Winterle, *J. Med. Chem.* 29 (1986), 2174-2183, P. Dubus, B. Decroix, J. Morel, P. Pastour, *Annales de Chimie (Paris, France)* 10 (1975) 331-336, and references above).

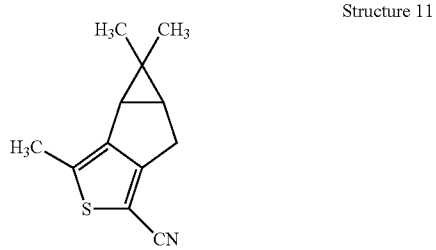

Structure 11

Depending on the nature of the functionalities present in the residues $R^1$ to $R^4$ in Structures 8, 10 and Formula (I), these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3rd Edition, Wiley New York, 1991; P. J. Kocienski, Protecting Groups, Thieme Stuttgart, 1994). Alternatively, the desired residues $R^1$ to $R^4$, in particular $R^3$, may also be introduced in later steps that follow the cyclisation of a compound of Structure 8 by performing the above reaction sequence with suitable precursors of the compounds of Structures 8 and 10, respectively. The compounds of Structure 10 or their precursors are either commercially available or are prepared according to procedures known to a person skilled in the art.

The compounds of Structure 11 may be prepared by reacting a compound of Structure 7 with the compound of Structure 12 in a solvent such as ethanol, methanol, THF, dioxane, DMF or mixtures thereof in the presence of a base such as aq. NaOH, aq. KOH, etc. at temperatures between 20 and 100° C. (in analogy to B. Hedegaard, J. Z. Mortensen, S. O. Lawesson, *Tetrahedron* 27 (1971), 3853-3859; and the preparation of a compound of Structure 5 above).

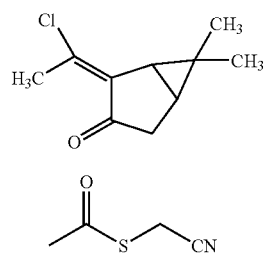

Structure 7

Structure 12

The (1S,5R)-isomer of 2-[1-chloro-ethylidene]-6,6-dimethyl-bicyclo[3.1.0]hexan-3-one ((1S,5R)-isomer of compound of Structure 7) may be prepared starting from commercially available (+)-3-carene according to the procedures given in the literature (e.g. S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243).

The racemic form of Structure 7 may be prepared starting from (+)-3-carene following the procedures given in the literature (W. Cocker, D. H. Grayson, *Tetrahedron Lett.* 51

(1969), 4451-4452; S. Lochynski; B. Jarosz, M. Walkowicz, K. Piatkowski, *J. Prakt. Chem.* (*Leipzig*) 330 (1988), 284-288; M. Walkowicz, H. Kuczynsky, C. Walkowicz, *Roczniki Chemii Ann. Soc. Chim. Polonorum* 41 (1967), 927-937; H. Kuczynski, M. Walkowicz, C. Walkowicz, K. Nowak, I. Z. Siemion, *Roczniki Chemii Ann. Soc. Chim. Polonorum,* 38 (1964), 1625-1633; A. V. Pol, V. G. Naik, H. R. Sonawane, *Ind. J. Chem. Sect. B,* 19 (1980) 603-604; S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243) and is exemplified below.

The compounds of the Formula (I) that base on the (1R, 5S)-isomer of 2-[1-chloro-ethylidene]-6,6-dimethyl-bicyclo[3.1.0]hexan-3-one ((1R, 5S)-isomer of compound of Structure 7) may be obtained by resolving the racemic mixture of a compound of Formula (I) or one of its precursors into its pure enantiomers by a method known per se to a person skilled in the art, preferably by chromatography or crystallisation.

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 m, 120 A, gradient: 5-95% acetonitrile in water, 1 min, with 0.04% trifluoroacetic acid, flow: 4.5 mL/min), $t_R$ is given in min; by TLC (TLC-plates from Merck, Silica gel 60 $F_{254}$); or by melting point. Compounds are purified by preparative HPLC (column: X-terra RP18, 50×19 mm, 5 μm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

ABBREVIATIONS approx. approximately
aq. Aqueous
atm atmosphere
BSA bovine serum albumin
CC column chromatography
DCC dicyclohexyl carbodiimide
DCM dichloromethane
DEAD diethylazodicarboxylate
DIPEA diisopropyl-ethylamine, Hünig's base, ethyl-diisopropylamine
DMF dimethylformamide
DMSO dimethylsulfoxide
EA ethyl acetate
EDC N-(3-dimethylaminopropyl)-N'-ethyl-carbodiimide
Et ethyl
h hour(s)
HMDS hexamethyldisilazane
HOBt 1-hydroxybenzotriazole
LC-MS liquid chromatography-mass spectrometry
min minute(s)
prep. preparative TBTU 2-(1H-benzotriazole-1-yl)-1,2,3,3-tetramethyluronium tetrafluoroborate
TFA trifluoroacetic acid
THF tetrahydrofuran
rt room temperature
sat. saturated
S1P sphingosine 1-phosphate
$t_R$ retention time
TLC thin layer chromatography (1aS,5aR)-1,1,2-Trimethyl-1,1a,5,5a-tetrahydro-3-thia-cyclopropa[a]pentalene-4-carboxylic acid ethyl ester (Compound of Structure 5)

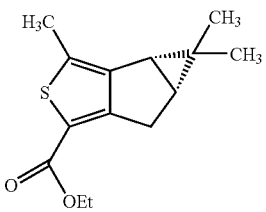

a) NaH (7.0 g, 60% dispersion in mineral oil, 175 mmol) is washed with pentane (100 mL) before it is suspended in THF (400 mL). The suspension is cooled to 0° C. and a solution of ethyl 2-mercaptoacetate (12.62 g, 105 mmol) in THF (50 mL) is added over a period of 20 min. The temperature of the reaction is maintained at 5-10° C. Upon completion of the addition, the cooling is removed and stirring is continued for 30 min. A solution of (1S, 5R)-2-(1-chloro-(E)-ethylidene)-6,6-dimethyl-bicyclo[3.1.0]hexan-3-one (S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243) (12.93 g, 70 mmol) in THF (50 mL) is added to the suspension and the resulting mixture is stirred for 1.5 h at rt. The mixture is filtered, the filtrate is concentrated to about 100 mL, diluted with 1 M aq. NaOH (100 mL) and extracted twice with DCM (150 mL). The extracts are dried over $Na_2SO_4$ and evaporated to furnish a crude E/Z mixture of {1-[(1S,5R)-6,6-dimethyl-3-oxo-bicyclo[3.1.0]hexylidene]-ethylsulfanyl}-acetic acid ethyl ester (18.2 g) as a brown oil. LC-MS: $t_R$=1.00 min, [M+1]$^+$=269.13. $^1$H NMR (CDCl$_3$): δ 4.22 (q, J=7.0 Hz, 2H both isomers), 3.67 (d, J=15.8 Hz, 1H major isomer), 3.63 (d, J=15.8 Hz, 1H minor isomer), 3.58 (d, J=15.8 Hz, 1H major isomer), 3.54 (d, J=15.8 Hz, 1H, minor isomer), 2.67 (dd, J=6.4, 19.4 Hz, 1H minor isomer), 2.60 (dd, J=7.0, 19.4 Hz, 1H major isomer), 2.58 (s, 3H minor isomer), 2.52 (s, 3H major isomer), 2.36-2.32 (m, 1H major isomer), 2.30-2.26 (m, 1H major isomer, 1H minor isomer), 2.18 (d, J=7.0 Hz, 1H minor isomer), 2.00 (d, J=7.0 Hz, 1H major isomer), 1.95 (d, J=7.6 Hz, 1H minor isomer), 1.30 (t, J=7.0 Hz, 3H major isomer), 1.28 (t, J=7.0 Hz, 3H minor isomer), 1.18 (s, 3H major isomer), 1.15 (s, 3H minor isomer), 0.89 (s, 3H minor isomer), 0.85 (s, 3H major isomer).

b) A solution of Na (1.70 g, 74.8 mmol) in abs. ethanol (75 mL) is heated to 60° C. before it is treated with a solution of crude {1-[(1S,5R)-6,6-dimethyl-3-oxo-bicyclo[3.1.0]hex-(2Z)-ylidene]-ethylsulfanyl}-acetic acid ethyl ester (18.2 g, 68.0 mmol) in abs. ethanol (200 mL). The mixture is stirred at 75° C. for 20 min, then cooled to rt, diluted with 0.5 M aq. NaOH (500 mL) and extracted with DCM (450+200 mL). The combined extracts are dried over Na$_2$SO$_4$, filtered and the solvent is removed in vacuo. This yields crude (1aS,5aR)-1, 1,2-trimethyl-1,1a,5,5a-tetrahydro-3-thia-cyclopropa[a]pentalene-4-carboxylic acid ethyl ester (10.5 g) as a yellow oil of 87% purity (LC-MS, UV 280 nm). LC-MS: $t_R$=1.11 min, [M+1]$^+$=251.14; $^1$H NMR (CDCl$_3$): δ 4.26 (q, J=7.0 Hz, 2H), 2.95 (dp, $J_d$=18.8 Hz, $J_p$=3.5 Hz, 1H), 2.79 (d, J=19.3, 1H), 2.37 (s, 3H), 1.89-1.84 (m, 2H), 1.34 (t, J=7.0 Hz, 3H), 1.12 (s, 3H), 0.72 (s, 3H).

(1aS,5aR)-1,1,2-Trimethyl-1,1a,5,5a-tetrahydro-3-thia-cyclopropa[a]pentalene-4-carboxylic acid (Compound of Structure 2)

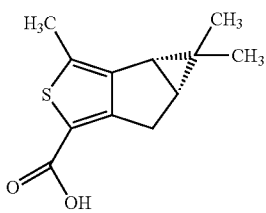

To a solution of crude (1aS,5aR)-1,1,2-trimethyl-1,1a,5,5a-tetrahydro-3-thia-cyclopropa[a]pentalene-4-carboxylic acid ethyl ester (10.3 g, 41.2 mmol) in ethanol (200 mL) a solution of 2N aq. LiOH (300 mL) is added. The resulting mixture is stirred at 70° C. for 1 h, cooled to rt and diluted with water (250 mL). The aq. solution is extracted three times with DCM (125 mL) before it is acidified to pH 3 by adding citric acid. The acidified solution is extracted twice with DCM (2×250 mL). These second extracts are combined, dried over Na$_2$SO$_4$, filtered and evaporated to leave (1aS,5aR)-1,1,2-trimethyl-1,1a,5,5a-tetrahydro-3-thia-cyclopropa[a]pentalene-4-carboxylic acid (7.0 g) as a yellow solid. LC-MS: $t_R$=0.95 min, [M+1]$^+$=223.00. $^1$H NMR (CDCl$_3$): δ3.04-2.92 (m, 1H), 2.83 (d, J=19.3 Hz, 1H), 2.39 (s, 3H), 1.91-1.87 (m, 2H), 1.13 (s, 3H), 0.73 (s, 3H).

Alternatively, (1aS,5a R)-1,1,2-trimethyl-1,1a,5,5a-tetrahydro-3-thia-cyclopropa[a]pentalene-4-carboxylic acid is also obtained by the following procedure: To a solution of sodium (2.80 g, 122 mmol) in ethanol (400 mL) a solution of mercapto-acetic acid ethyl ester (14.64 g, 122 mmol) in ethanol (40 mL) is added. The solution is stirred for 5 min before (1S, 5R)-2-(1-chloro-(E)-ethylidene)-6,6-dimethyl-bicyclo[3.1.0]hexan-3-one (15.0 g, 81.2 mmol) in ethanol (40 mL) is added dropwise. The solution becomes slightly warm (approx. 30° C.) and turns orange to brown. A fine precipitate forms. Stirring is continued at rt for 1 h. Then, a solution of sodium (2.24 g, 97.5 mmol) in ethanol (75 mL) is added rapidly and the mixture is heated to 75° C. for 1 h. A 2N aq. solution of LiOH (75 mL) is added and stirring is continued at 75° C. for 2 h, then at rt for 16 h. About ⅔ of the solvent is removed in vacuo, the remaining mixture is diluted with water (250 mL) and extracted with DCM (200 mL). The organic extract is washed twice with 1 N aq. (100 mL). The combined aqueous layers are acidified by adding 2N aq. HCl and extracted three times with diethyl ether (3×300 mL). The organic extracts are dried over MgSO$_4$ and evaporated. The remaining residue is suspended in acetonitrile, filtered, washed with additional acetonitrile and dried under high vacuum to give the title compound (12.02 g) as a pale yellow to beige crystalline powder.

rac-(1S,5R)-2-[1-Chloro-eth-(E)-ylidene]-6,6-dimethyl-bicyclo[3.1.0]hexan-3-one (Compound of Structure 7)

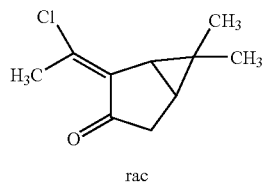

a) To a suspension of (+)-3-carene (82 g, 0.6 mol) and CaCO$_3$ (80 g, 0.8 mol) in water (300 mL) and dioxan (600 mL) is added N-bromosuccinimide (142 g, 0.8 mol). The mixture is stirred at rt for 1 h, diluted with water (1500 mL) and extracted with diethyl ether (500 mL). The organic extract is washed with water (3×1000 mL) and 5% aq. Na$_2$S$_2$O$_3$ (2×500 mL), and dried over Na$_2$SO$_4$. The solvent is removed under reduced pressure and the crude product is purified by column chromatography on silica gel eluting with hexane/EA 4:1 to yield (1S,3R,4R,6R)-4-bromo-3,7,7-trimethyl-bicyclo[4.1.0]heptan-3-ol (48.3 g) as a beige solid. $^1$H NMR (CDCl$_3$): δ 4.05 (dd, J=7.6, 10.6 Hz, 1H), 2.48-2.36 (m, 2H), 2.20 (dd, J=10.0, 14.7 Hz, 1H), 1.42-1.38 (m, 1H), 1.36 (s, 3H), 1.02 (s, 3H), 0.98 (s, 3H), 0.90-0.80 (m, 1H), 0.72-0.66 (m, 1H).

b) To a solution of (1S,3R,4R,6R)-4-bromo-3,7,7-trimethyl-bicyclo[4.1.0]heptan-3-ol (58.0 g, 0.25 mol) in water (120 mL) and dioxane (1600 mL) is added Ag$_2$O (156.4 g, 0.675 mol). The resulting suspension is stirred at rt for 18 h before it is filtered over celite. The filtrate is evaporated under reduced pressure. The remaining solid is dissolved in diethyl ether (650 mL) and washed with water (2×1000 mL). The organic extract is dried over Na$_2$SO$_4$ and the solvent is removed in vacuo to furnish 1-((1S,3S,5R)-6,6-dimethyl-bicyclo[3.1.0]hex-3-yl)-ethanone (36.6 g) as a pale yellow oil. $^1$H NMR (CDCl$_3$: δ 2.83-2.70 (m, 1H), 2.14-2.03 (m, 5H), 1.82 (dd, J=10.0, 14.1 Hz, 2H), 1.16-1.13 (m, 2H), 0.95 (s, 6H).

c) To a solution of 1-((1S,3S,5R)-6,6-dimethyl-bicyclo[3.1.0]hex-3-yl)-ethanone (36.5 g, 0.24 mol) in DCM (700 mL) is added 70% m-chloroperbenzoic acid (77 g, 0.312 mol) in portions. The reaction mixture is stirred at rt for 36 h before it is washed with 0.2 N aq. NaOH (1000 mL). The wash solution is extracted back with DCM (2×300 mL). The combined organic extracts are dried over MgSO$_4$ and the solvent is removed in vacuo to furnish acetic acid (1S,3S,5R)-6,6-dimethyl-bicyclo[3.1.0]hex-3-yl ester (37.8 g) as a pale yellow oil. $^1$H NMR (CDCl$_3$): δ 4.94 (hept. J=3.5 Hz, 1H), 2.02-1.93 (m, 5H), 1.87-1.78 (m, 2H), 1.22-1.15 (m, 2H), 0.95 (s, 3H), 0.83 (s, 3H).

d) A solution of acetic acid (1S,3S,5R)-6,6-dimethyl-bicyclo[3.1.0]hex-3-yl ester (37.85 g, 225 mmol) in ethanol (700 mL) is treated with 2 N aq. LiOH (700 mL). The mixture is stirred at rt for 1 h, diluted with water (600 mL) and extracted with EA (2×150 mL). The combined organic extracts are dried over MgSO$_4$ and evaporated to give (1S,3S,5R)-6,6-dimethyl-bicyclo[3.1.0]hexan-3-ol (23.9 g) as a pale yellow oil. $^1$H NMR (CDCl$_3$): δ 4.23 (hept, J=2.9 Hz, 1H), 1.87-1.70 (m, 4H), 1.23-1.20 (m, 2H), 0.96 (s, 3H), 0.81 (s, 3H).

e) To a mixture of pyridine (80 mL) and DCM (720 mL) is added CrO$_3$ (50 g, 0.5 mol). The mixture is stirred for 5 min before (1S,3S,5R)-6,6-dimethyl-bicyclo[3.1.0]hexan-3-ol (11.5 g, 0.08 mol) is added. Stirring is continued at rt for 2.5 h. The mixture is decanted from an oily residue, diluted with DCM (100 mL) and washed with 2 N aq. HCl (3×80 mL) followed by sat. aq. NaHCO$_3$ solution (80 mL). The separated organic phase is dried over NaSO$_4$ and the solvent is removed in vacuo to give (1S,5R)-6,6-dimethyl-bicyclo[3.1.0]hexan-3-one as a pale yellow oil. $^1$H NMR (CDCl$_3$): δ 2.58-2.46 (m, 2H), 2.19-2.11 (m, 2H), 1.34-1.26 (m, 2H), 1.09 (s, 3H), 0.87 (s, 3H).

f) To a suspension of NaH (873 mg 55% dispersion in mineral oil, 20 mmol, washed with dioxane prior to use) in dioxane (15 mL) is added methyl acetate (2.22 g, 30 mmol). The suspension is stirred for 5 min at rt and a solution of (1S,5R)-6,6-dimethyl-bicyclo[3.1.0]hexan-3-one (1.24 g, 10 mmol) in dioxane (5 mL) is added. The reaction mixture is stirred at 65° C. overnight. The mixture is poured onto cold 10% aq. citric acid solution (75 mL) and extracted with DCM (3×75 mL). The organic extracts are washed with water, dried over MgSO$_4$ and evaporated to give crude racemic (1R, 2R, 5R)-2-acetyl-6,6-dimethyl-bicyclo[3.1.0]hexan-3-one (2.45 g, contains dioxane) as a dark yellow liquid. $^1$H NMR (CDCl$_3$): δ 2.61 (dd, J=7.3, 19.6 Hz, 1H), 2.34-2.20 (m, 1H), 2.01 (s, 3H), 1.72 (d, J=8.2 HZ, 1H), 1.40-1.20 (m, 2H), 1.09 (s, 3H), 0.81 (s, 3H).

g) A mixture of the above yellow liquid (1.66 g, 10 mmol), triphenylphosphine (4.53 g, 17 mmol) and CCl$_4$ (5 mL) in chloroform (15 mL) is heated to 65° C. for 1 h. The mixture is concentrated and the remaining residue is stirred with pentane. The pentane is decanted and the remaining residue is once more treated with pentane. The pentane fractions are combined and concentrated to leave rac-(1S,5R)-2-[1-chloro-eth-(E)-ylidene]-6,6-dimethyl-bicyclo[3.1.0]hexan-3-one (1.9 g) as brownish oil. This material is used in the next step without further purification. LC-MS: $t_R$=1.02 min.

(1aS,5aR)-1,1,2-Trimethyl-1,1a,5,5a-tetrahydro-3-thia-cyclopro-pa[a]pentalene-4-carbonitrile (Compound of Structure 11)

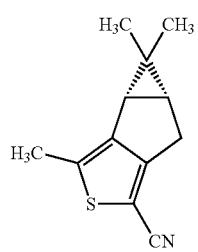

A solution of (1S, 5R)-2-(1-chloro-(E)-ethylidene)-6,6-dimethyl-bicyclo[3.1.0]hexan-3-one (997 mg, 5.40 mmol) and thioacetic acid S-cyanomethyl ester (746 mg, 6.48 mmol) in THF (37 mL) is treated with 2 N aq. NaOH (10.8 mL). The resulting mixture is stirred vigorously at rt for 2 h. Another portion of thioacetic acid S-cyanomethyl ester (100 mg, 0.87 mmol) and 2 N aq. NaOH (2 mL) is added and stirring is continued for 1 h. The reaction mixture is diluted with 2 N aq. NaOH and extracted twice with DCM. The organic extracts are dried over Na$_2$SO$_4$ and evaporated. The remaining brown oil is dissolved in THF (30 mL) and treated with 2 N aq. NaOH (3 mL). The mixture is heated to 90° C. for 4 h before it is diluted with 2 N aq. NaOH and extracted with DCM. The organic extracts are dried over Na$_2$SO$_4$ and evaporated. The crude product is purified by prep. HPLC (Phenomenex Aqua 30×75 mm, gradient 10 to 95% acetonitrile in water containing 0.5% formic acid) to give (1aS,5aR)-1,1,2-trimethyl-1,1a,5,5a-tetrahydro-3-thia-cyclopro-pa[a]pentalene-4-carbonitrile (650 mg) as a brown oil; LC-MS: $t_R$=1.06 min, [M+1+CH$_3$CN]$^+$=245.11; $^1$H NMR (CDCl$_3$): δ 2.90 (dd, J=5.9, 18.8 Hz, 1H), 2.68 (d, J=18.8 Hz, 1H), 2.38 (s, 3H), 1.96-1.88 (m, 2H), 1.13 (s, 3H), 0.72 (s, 3H).

(1aS,5aR)-N-Hydroxy-1,1,2-trimethyl-1,1a,5,5a-tetrahydro-3-thia-cyclopropa[a]pentalene-4-carboxamidine (compound of Structure 9)

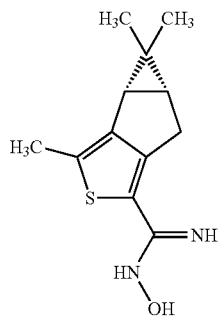

To a stirred suspension of K-tert.-butylate (281 mg, 2.5 mmol), hydroxylamine hydrochloride (208 mg, 3.0 mmol) in methanol (4 mL) is added (1aS,5aR)-1,1,2-trimethyl-1,1a,5,5a-tetrahydro-3-thia-cyclopro-pa[a]pentalene-4-carbonitrile (203 mg, 1.0 mmol). The reaction mixture is stirred at rt for 5 h before it is filtered. The filtrate is purified by prep. HPLC (Water XTerrra Prep MS C18 30×75 mm, 10% to 95% acetonitrile in water containing 0.5% sat. aq. NH$_3$) to give (1aS,5aR)-N-hydroxy-1,1,2-trimethyl-1,1a,5,5a-tetrahydro-3-thia-cyclopropa[a]pentalene-4-carboxamidine (200 mg) as a colourless solid; LC-MS: $t_R$=0.72 min, [M+1]$^+$=237.09.

Methanesulfonic acid 2,2-dimethyl-[1,3]dioxan-5-ylmethyl ester

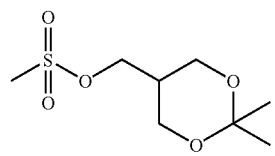

The title compound is prepared following the procedures given in B. Xu, A. Stephens, G. Kirschenheuter, A. F. Greslin, X. Cheng, J. Sennelo, M. Cattaneo, M. L. Zighetti, A. Chen, S.-A. Kim, H. S. Kim, N. Bischofberger, G. Cook, K. A. Jacobson, *J. Med. Chem.* 45 (2002) 5694-5709.

Example 1

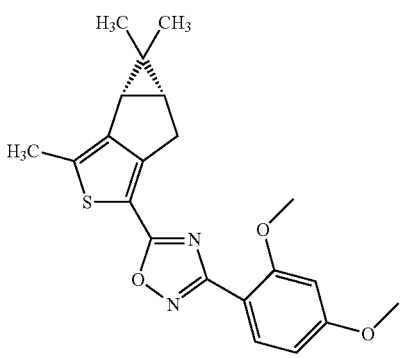

a) A mixture of 2,4-dimethoxybenzonitrile (3.25 g, 20 mmol), hydroxylamine hydrochloride (2.92 g, 42 mmol) and K$_2$CO$_3$ (5.80 g, 42 mmol) in ethanol (80 mL) is stirred at 85° C. for 27 h before it is poured onto water (250 mL). The solution is acidified by adding 1 N aq. HCl (75 mL) and extracted once with DCM (100 mL). The aq. layer is basified with 1 N aq. NaOH (90 mL) and extracted three times with DCM (3×150 mL). The organic extracts are dried over MgSO$_4$, the solvent is evaporated and the residue is dried under high vacuum to leave N-hydroxy-2,4-dimethoxy-benzamidine (1.35 g) as a beige solid. LC-MS: t$_R$=0.68 min, [M+1]$^+$=197.11.

b) A mixture of N-hydroxy-2,4-dimethoxy-benzamidine (98 mg, 0.50 mmol), (1aS,5aR)-1,1,2-trimethyl-1,1a,5,5a-tetrahydro-3-thia-cyclopropa[a]pentalene-4-carboxylic acid (111 mg, 0.50 mmol), TBTU (178 mg, 0.55 mmol) and DIPEA (646 mg, 5 mmol) in DMF (4 mL) is stirred at rt for 45 min, then at 110° C. for 1 h. The reaction mixture is directly subjected to prep. HPLC purification (Phenomenex Aqua 75×30 mm, gradient with acetonitrile/water containing 0.5% formic acid) to give 3-(2,4-dimethoxy-phenyl)-5-((1aS,5aR)-1,1,2-trimethyl-1,1a,5,5a-tetrahydro-3-thia-cyclopropa[a]pentalen-4-yl)-[1,2,4]oxadiazole (19 mg) as a colourless lyophilisate; LC-MS: t$_R$=1.17 min, [M+1]$^+$=383.13; $^1$H NMR (CDCl$_3$): δ 7.89 (d, J=8.8 Hz, 1H), 6.46 (dd, J=2.3, 8.8 Hz, 1H), 6.43 (d, J=2.3 Hz, 1H), 3.83 (s, 3H), 3.74 (s, 3H), 2.96 (dd, J=5.9, 18.8 Hz, 1H), 2.80 (d, J=18.8 Hz, 1H), 2.29 (s, 3H), 1.88-1.78 (m, 2H), 1.02 (s, 3H), 0.63 (s, 3H).

Example 2

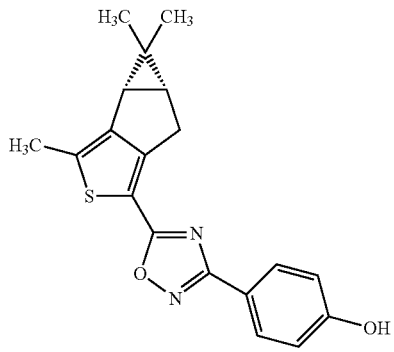

a) To dry methanol (285 mL) is carefully added K-tert.-butylate (28.28 g, 252 mmol) followed by hydroxylamine hydrochloride (15.0 g, 216 mmol). The suspension is stirred for 30 min before 4-hydroxybenzonitrile (8.58 g, 72 mmol) is added. The mixture is refluxed for 40 h, the solvent is evaporated and the residue is acidified by adding 2 N aq. HCl. The solution is extracted twice with DCM (100 mL). The aq. layer is basified by adding solid NaHCO$_3$. The product precipitates, is filtered off, washed with water and dried to give 4,N-dihydroxy-benzamidine (7.6 g) as a brownish solid; $^1$H NMR (D$_6$-DMSO): δ 9.57 (s, 1H), 9.33 (s, 1H), 7.48-7.42 (m, 2H), 6.74-6.68 (m, 2H), 5.62 (s, 2H).

b) A solution of (1aS,5aR)-1,1,2-trimethyl-1,1a,5,5a-tetrahydro-3-thia-cyclopropa[a]pentalene-4-carboxylic acid (3.50 g, 15.74 mmol), TBTU (5.56 g, 17.32 mmol) and DIPEA (8.89 mL, 51.96 mmol) in DMF (35 mL) is stirred for 10 min at rt before 4,N-dihydroxy-benzamidine (2.64 g, 17.32 mmol) is added. The solution is stirred for further 30 min, formic acid is added (7 mL) and the solution is chromatographed by prep. HPLC (Grom-Sil 120 ODS-4-HE, 30×75 mm, gradient with acetonitrile/water containing 0.5% formic acid) to give (1aS,5aR)-1,1,2-trimethyl-1,1a,5,5a-tetrahydro-3-thia-cyclopropa[a]pentalene-4-carboxylic acid N-(4-hydroxy-(hydroxybenzamidine)) ester (4.5 g) as a colourless solid, LC-MS: t$_R$=0.97 min, [M+1]$^+$=357.14.

c) A suspension of (1aS,5aR)-1,1,2-trimethyl-1,1a,5,5a-tetrahydro-3-thia-cyclopropa[a]pentalene-4-carboxylic acid N-(N-hydroxy-4-hydroxy-benzamidine) ester (4.5 g, 12.63 mmol) in toluene (450 mL) is stirred at 105° C. for 48 h before the solvent is removed under reduced pressure. The residue is dissolved in acetonitrile/methanol and purified by prep. HPLC (Grom-Sil 120 ODS-4-HE, 30×75 mm, gradient with acetonitrile/water containing 0.5% formic acid) to give 4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol (2.9 g) as a colourless solid; LC-MS: t$_R$=1.11 min, [M+1]$^+$=339.13; $^1$H NMR (CDCl$_3$): δ 8.04-7.98 (m, 2H), 6.94-6.89 (m, 2H), 5.37 (s br, 1H), 3.10 (dd, J=5.7, 18.8 Hz, 1H), 2.93 (d, J=18.8 Hz, 1H), 2.43 (s, 3H), 2.00-1.92 (m, 2H), 1.14 (s, 3H), 0.75 (s, 3H).

Examples 3 to 12

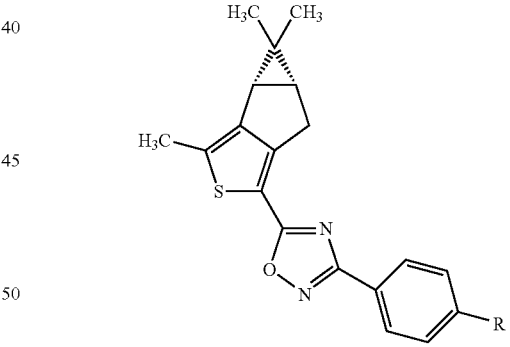

To a solution of 4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol (10 mg, 0.03 mmol) in isopropanol (1 mL) the corresponding alkylating agent (as bromide, chloride or mesylate) (0.15 mmol) and 2 N aq. NaOH (0.2 mL) are added. The reaction mixture is shaken for 8 h at 70° C. The reaction mixtures are purified by prep. HPLC (either Waters XTerra Prep MS C18 19×50 mm 5 μm, 90% to 5% water (0.8% NEt$_2$)/acetonitrile or Waters Symmetry C18 19×50 mm 5 um, 90% to 5% water (0.5% HCOOH)/acetonitrile) to give the desired products as colourless lyophilisates. In the case of Example 8 the reaction mixture is shaken for 8 h at 85° C. before TFA (0.3 mL) is added. The mixture is shaken for another hour at 60° C. prior to purification by prep. HPLC.

| Example | R | Scale (mmol) | LC-MS $t_R$ (min) | [M + H]⁺ |
|---|---|---|---|---|
| 3 | O~~~OH | 0.03 | 1.12 | 383.11 |
| 4 | O~~~OH (with CH₃) | 0.03 | 1.15 | 397.17 |
| 5 | O~~~OH with OH | 0.03 | 1.04 | 413.16 |
| 6 | O~~~OH with OH | 0.03 | 1.04 | 413.17 |
| 7 | O~~~O~ with OH | 0.03 | 1.13 | 427.16 |
| 8 | O~~~OH with OH | 0.03 | 1.07 | 427.09 |
| 9 | O~~~~OH | 0.03 | 1.04 | 413.16 |
| 10 | O~~N(CH₃)₂ | 0.03 | 1.15 | 397.16 |
| 11 | O~~N-pyrrolidine | 0.03 | 0.95 | 436.25 |
| 12 | O~~N-morpholine | 0.03 | 0.93 | 452.20 |

Example 13

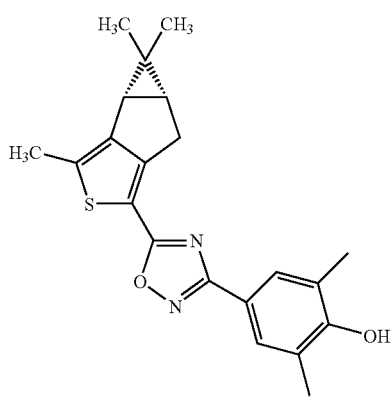

a) To dry methanol (190 mL) is carefully added K-tert.-butylate (18.68 g, 166 mmol) followed by hydroxylamine hydrochloride (9.92 g, 143 mmol). The suspension is stirred for 30 min before 3,5-dimethyl-4-hydroxybenzonitrile (7.00 g, 147 mmol) is added. The mixture is refluxed for 32 h, then the suspension is diluted by adding 2 N aq. HCl. The solution is extracted twice with DCM (100 mL). The aq. layer is basified (pH 9) by adding solid NaHCO₃ and extracted five times with DCM followed by four times with EA. The combined organic layers are dried over $Na_2SO_4$ and evaporated to dryness to give 4,N-dihydroxy-3,5-dimethyl-benzamidine (7.9 g) as a colourless solid; LC-MS: $t_R$=0.62 min, [M+1]⁺=181.14.

b) A solution of (1aS,5aR)-1,1,2-trimethyl-1,1a,5,5a-tetrahydro-3-thia-cyclopropa[a]pentalene-4-carboxylic acid (3.00 g, 13.50 mmol), TBTU (4.77 g, 14.85 mmol) and DIPEA (7.62 mL, 44.53 mmol) in DMF (30 mL) is stirred for 10 min at rt before 4,N-dihydroxy-3,5-dimethyl-benzamidine (2.68 g, 14.85 mmol) is added. The solution is stirred for further 20 min, formic acid (6 mL) is added and the solution is chromatographed by prep. HPLC (Grom-Sil 120 ODS-4-HE, 30×75 mm, gradient with acetonitrile/water containing 0.5% formic acid) to give (1aS,5aR)-1,1,2-trimethyl-1,1a,5,5a-tetrahydro-3-thia-cyclopropa[a]pentalene-4-carboxylic acid N-(3,5-dimethyl-4-hydroxy-benzamidine) ester (4.1 g) as a colourless solid; LC-MS: $t_R$=1.03 min, [M+1]⁺=385.18; ¹H NMR (D₆-DMSO): δ 8.65 (s, 1H), 7.30 (s, 2H), 6.38 (s br, 2H), 3.04 (dd, J=5.9, 18.8 Hz, 1H), 2.75 (d, J=18.8 Hz, 1H), 2.36 (s, 3H), 2.18 (s, 6H), 2.01-1.88 (m, 2H), 1.10 (s, 3H), 0.70 (s, 3H).

c) A suspension of (1aS,5aR)-1,1,2-trimethyl-1,1a,5,5a-tetrahydro-3-thia-cyclopropa[a]pentalene-4-carboxylic acid N-(3,5-dimethyl-4-hydroxy-benzamidine) ester (4.0 g, 10.41 mmol) in toluene (400 mL) is stirred at 100° C. for 24 h before the solvent is removed under reduced pressure. The residue is dissolved in DCM and purified by column chromatography on silica gel eluting with hexane:EA 5:1 to give 2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol (1.5 g) as a colourless solid; LC-MS: $t_R$=1.37 min, [M+1]⁺=367.13; ¹H NMR (CDCl₃): δ 7.75 (s, 2H), 4.90 (s, 1H), 3.12 (dd, J=5.9, 18.8 Hz, 1H), 2.94 (d, J=18.8 Hz, 1H), 2.44 (s, 3H), 2.32 (s, 6H), 2.02-1.94 (m, 2H), 1.16 (s, 3H), 0.77 (s, 3H).

Examples 14 to 18 and 20 to 23

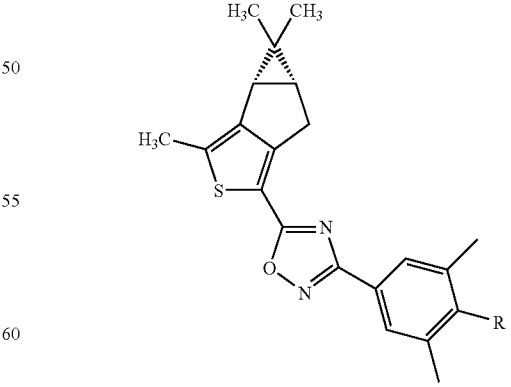

To a solution of 2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol (10 mg, 0.027 mmol) in isopropanol (1 mL) the corresponding alkylating agent (as bromide, chloride or mesylate) (0.135 mmol) and 2 N aq. NaOH (0.2 mL) are added. The reaction mixture is shaken for 10 h at 65° C. The reaction mixtures are purified by prep. HPLC (Waters XTerra Prep MS C18 19×50 mm 5 um, 80% to 5% water (0.85% NEt$_2$)/Acetonitrile) to give the desired products as colourless lyophilisates.

| Example | R | Scale (mmol) | LC-MS $t_R$ (min) | [M + H]$^+$ |
|---|---|---|---|---|
| 14 | O~~~OH | 0.027 | 1.17 | 411.26 |
| 15 | O~~~OH (with methyl) | 0.027 | 1.20 | 425.26 |
| 16 | O~~~OH, OH (stereo) | 0.027 | 1.09 | 441.21 |
| 17 | O~~~OH, OH (stereo) | 0.027 | 1.09 | 441.24 |
| 18 | O~~~O~, OH | 0.027 | 1.19 | 455.27 |
| 20 | O~~~~OH | 0.027 | 1.20 | 425.19 |
| 21 | O~~~N(CH$_3$)$_2$ | 0.027 | 0.97 | 438.21 |
| 22 | O~~~N-pyrrolidine | 0.027 | 1.00 | 464.32 |
| 23 | O~~~N-morpholine | 0.027 | 0.98 | 480.29 |

Example 14

$^1$H NMR (CDCl$_3$): δ 7.78 (s, 2H), 4.00-3.90 (m, 4H), 3.12 (dd, J=5.9, 18.8 Hz, 1H), 2.94 (d, J=18.8 Hz, 1H), 2.43 (s, 3H), 2.36 (s, 6H), 2.14 (t br, J=5 Hz, 1H), 2.01-1.92 (m, 2H), 1.15 (s, 3H), 0.76 (s, 3H).

Example 16

$^1$H NMR (CDCl$_3$): δ 7.78 (s, 2H), 4.17-4.08 (m, 1H), 3.94-3.80 (m, 4H), 3.11 (dd, J=5.9, 18.8 Hz, 1H), 2.94 (d, J=18.8 Hz, 1H), 2.72 (d br, J=3.5 Hz, 1H), 2.43 (s, 3H), 2.35 (s, 6H), 2.06 (s br, 1H), 2.01-1.90 (m, 2H), 1.14 (s, 3H), 0.76 (s, 3H).

Example 20

$^1$H NMR (CDCl$_3$): δ7.78 (s, 2H), 4.01-3.92 (m, 4H), 3.11 (dd, J=5.9, 18.8 Hz, 1H), 2.94 (d, J=18.8 Hz, 1H), 2.43 (s, 3H), 2.35 (s, 6H), 2.14-2.03 (m, 2H), 2.00-1.91 (m, 3H), 1.15 (s, 3H), 0.76 (s, 3H).

Example 19

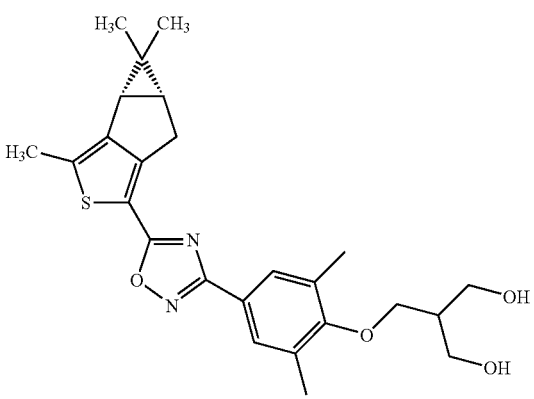

a) To a solution of triphenylphosphine (161 mg, 0.615 mmol) in dry THF is added DEAD (0.097 mL, 0.615 mmol). The solution is stirred at rt for 1 h before (2,2-dimethyl-[1,3]dioxan-5-yl)-methanol (90 mg, 0.615 mmol) and 2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol (150 mg, 0.410 mmol) is added. Stirring is continued for 24 h. The reaction mixture is purified by prep. HPLC (Waters XTerra Prep MS C18 19×50 mm 5 μm, water (0.85% NEt$_2$)/acetonitrile) to give 3-[4-(2,2-dimethyl-[1,3]dioxan-5-ylmethoxy)-3,5-dimethyl-phenyl]-5-((1aS,5aR)-1,1,2-trimethyl-1,1a,5,5a-tetrahydro-3-thia-cyclopropa[a]pentalen-4-yl)-[1,2,4]oxadiazole (135 mg) as colourless lyophilisate; LC-MS: $t_R$=1.29 min, [M+1]$^+$=495.30.

b) A suspension of 3-[4-(2,2-dimethyl-[1,3]dioxan-5-ylmethoxy)-3,5-dimethyl-phenyl]-5-((1aS,5aR)-1,1,2-trimethyl-1,1a,5,5a-tetrahydro-3-thia-cyclopropa[a]pentalen-4-yl)-[1,2,4]oxadiazole (135 mg, 0.273 mmol) in acetic acid/water 4:1 (4 mL) and THF (2 mL) is stirred at rt for 3 h. Then, approx. 6 N HCl in isopropanol (1 mL) is added and stirring is continued for 30 min. Diethylamine (0.2 mL) is added to the mixture which is then purified by prep. HPLC (Grom-Sil 120 ODS-4-HE, 30×75 mm, 10 um, acetonitile/water (0.5% HCOOH), 20% to 95% acetonitrile) to give 2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-propane-1,3-diol (50 mg) as a colourless resin; LC-MS: $t_R$=1.12 min, [M+1]$^+$=455.22; $^1$H NMR (CDCl$_3$): δ 7.78 (s, 2H), 4.05-4.00 (m, 4H), 3.98-3.94 (m, 2H), 3.11 (dd, J=6.4, 18.8 Hz, 1H), 2.94 (d, J=18.8 Hz, 1H), 2.43 (s, 3H), 2.35 (s, 6H), 2.32-2.23 (m, 1H), 2.14 (s br, 2H), 2.00-1.92 (m, 2H), 1.15 (s, 3H), 0.76 (s, 3H).

Examples 24 to 34, 36 and 37

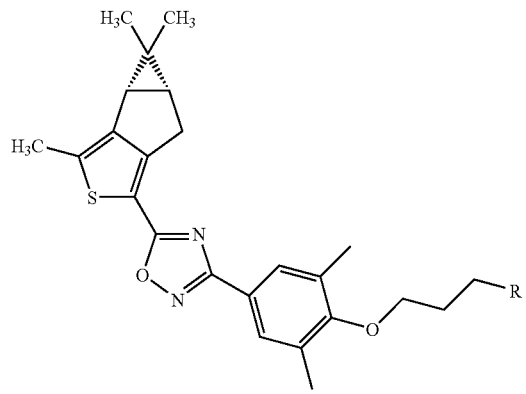

a) To a solution of 2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol (250 mg, 0.68 mmol) in isopropanol (6.8 mL) and 2 N aq. NaOH (2.3 mL) 3-bromoethanol (0.12 mL, 1.42 mmol) is added. The reaction mixture is stirred for 13 h at 65° C. The solution is poured onto 0.5 N aq. HCl and extracted twice with DCM. The organic extracts are dried over MgSO₄ and evaporated. The crude product is purified by column chromatography on silica gel eluting with DCM:TBME 22:1 to give 3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-1-ol (170 mg, Example 20) as a beige resin; LC-MS: $t_R$=1.20 min, [M+1]$^+$=425.20.

b) At 0° C., a solution of 3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-1-ol (170 mg, 0.40 mmol) and DIPEA (0.11 mL, 0.64 mmol) in DCM (5 mL) is treated with methanesulfonyl chloride (0.04 mL, 0.48 mmol). The reaction mixture is stirred at 0° C. for 30 min, then at rt for 1 h before it is diluted with DCM (15 mL) and washed with 0.1 N aq. NaOH (20 mL) followed by 10% aq. citric acid solution (20 mL). The organic layer is dried over Na₂SO₄ and evaporated to dryness to give methanesulfonic acid 3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl ester (185 mg) as a beige resin; LC-MS: $t_R$=1.23 min, [M+1]$^+$=503.20.

c) A mixture of methanesulfonic acid 3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl ester (9 mg, 0.017 mmol), the corresponding amine (0.067 mmol) and DIPEA (0.025 mL) in DMF is shaken at 85° C. for 7 h. The reaction mixture is subjected to prep. HPLC purification (Waters Xterra MS18 19×50 mm 5 um, 90% to 5% 0.1 N aq. HCl/acetonitrile) to give the desired products as colourless lyophilisates.

| Example | R | Scale (mmol) | $t_R$ (min) | [M + H]$^+$ |
|---|---|---|---|---|
| 24 | NH₂ | 0.017 | 0.96 | 424.24 |
| 25 | NHCH₃ | 0.017 | 0.98 | 438.30 |
| 26 | N(CH₃)₂ | 0.017 | 0.99 | 452.31 |
| 27 | HN~~~OH | 0.017 | 0.95 | 468.26 |
| 28 | pyrrolidinyl | 0.017 | 1.02 | 478.35 |
| 29 | HN-propyl | 0.017 | 1.02 | 466.33 |
| 30 | HN-CH(CH₂OH)₂ | 0.017 | 0.94 | 498.30 |
| 31 | HN~~~NH₂ | 0.017 | 0.85 | 467.32 |
| 32 | HOOC-prolinyl | 0.017 | 1.03 | 522.31 |
| 33 | 3-COOH-pyrrolidinyl | 0.017 | 1.01 | 522.32 |
| 34 | piperazinyl-CH₂CH₂OH | 0.017 | 0.88 | 537.39 |
| 36 | HN-iPr | 0.017 | 1.01 | 466.25 |
| 37 | HN~~~O~CH₃ | 0.017 | 1.04 | 511.33 |

Example 27

As Hydrochloride $^1$H NMR (D₆-DMSO): δ 8.81 (s br, 2H), 7.67 (s, 2H), 5.25 (t br, J=5 Hz, 1H), 3.88 (t, J=5.9 Hz, 2H), 3.71-3.64 (m, 2H), 3.20-3.00 (m, 5H), 2.84 (d, J=18.8 Hz, 1H), 2.41 (s, 3H), 2.30 (s, 6H), 2.18-1.96 (m, 4H), 1.10 (s, 3H), 0.70 (s, 3H).

Example 35

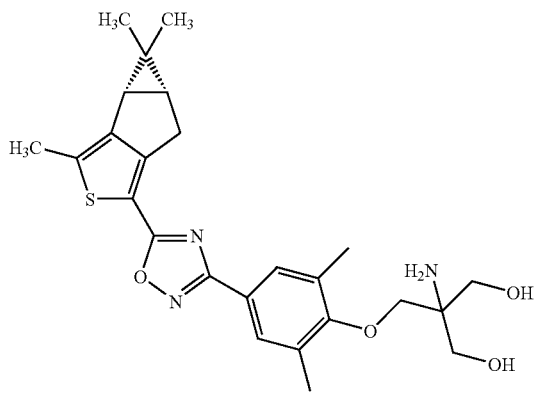

a) To a solution of triphenylphosphine (161 mg, 0.615 mmol) in dry THF (2.5 mL) is added DEAD (0.097 mL, 0.615 mmol). The solution is stirred at rt for 1 h before (2,2-dimethyl-5-nitro-[1,3]dioxan-5-yl)-methanol (118 mg, 0.615 mmol) and 2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol (150 mg, 0.410 mmol) is added. Stirring is continued for 7 days. The formed precipitate is collected, washed with isopropanol and dried under high vacuum to give 3-[4-(2,2-dimethyl-5-nitro-[1,3]dioxan-5-ylmethoxy)-3,5-dimethyl-phenyl]-5-((1aS,5aR)-1,1,2-trimethyl-1,1a,5,5a-tetrahydro-3-thia-cyclopropa[a]pentalen-4-yl)-[1,2,4]oxadiazole (90 mg) as an almost colourless solid; LC-MS: $t_R$=1.30 min, $[M+1]^+$=540.28; $^1$H NMR (CDCl$_3$): δ 7.77 (s, 2H), 4.50 (d, J=12.9 Hz, 2H), 4.29-4.21 (m, 4H), 3.10 (dd, J=6.4, 18.8 Hz, 1H), 2.93 (d, J=18.8 Hz, 1H), 2.43 (s, 3H), 2.28 (s, 6H), 2.00-1.91 (m, 2H), 1.48 (s, 3H), 1.45 (s, 3H), 1.15 (s, 3H), 0.76 (s, 3H).

b) A suspension of 3-[4-(2,2-dimethyl-5-nitro-[1,3]dioxan-5-ylmethoxy)-3,5-dimethyl-phenyl]-5-((1aS,5aR)-1,1,2-trimethyl-1,1a,5,5a-tetrahydro-3-thia-cyclopropa[a]pentalen-4-yl)-[1,2,4]oxadiazole (85 mg, 0.158 mmol) in THF:TFA:water 20:4:1 (12.5 mL) is stirred at 65° C. for 4.5 h. The mixture is further diluted with TFA:water 2:1 (1.5 mL) and stirring is continued at 65° C. for 3 h. The mixture is cooled to rt, poured onto 2N aq. NaOH and extracted twice with DCM. The organic extracts are dried over MgSO$_4$ and evaporated to give 2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-2-nitro-propane-1,3-diol (78 mg) as a beige resin; LC-MS: $t_R$=1.17 min, $[M+1]^+$=500.89.

c) A solution of 2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-2-nitro-propane-1,3-diol (75 mg, 0.151 mmol) in acetonitrile (9 mL), TFA (4 mL) and water (0.5 mL) is treated with Zn (200 mg, 3.06 mmol). The suspension is stirred at 65° C. for 1 h before another portion of Zn (100 mg, 1.53 mmol) is added. Stirring is continued at 65° C. for 45 min. The mixture is filtered and the filtrate is poured onto 2 N aq. NaOH and extracted three times with DCM. The organic extracts are dried over MgSO$_4$ and evaporated. The crude product is purified by prep. HPLC (Water Symmetry C18, 19×50 mm, gradient 95% water (0.5% formic acid) to 95% acetonitrile) to yield 2-amino-2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-propane-1,3-diol hydrochloride (23 mg) as a colourless powder after evaporation of the isolated product from a mixture of methanol (9 mL) and 6 N HCl in isopropanol (1 mL); LC-MS: $t_R$=0.89 min, $[M+1]^+$=470.26; $^1$H NMR (D$_6$-DMSO): δ 8.18 (s br, 3H), 7.69 (s, 2H), 5.47 (s br, 2H), 3.87 (s, 2H), 3.71 (s, 4H), 3.07 (dd, J=5.9, 18.8 Hz, 1H), 2.84 (d, J=18.8 Hz, 1H), 2.42 (s, 3H), 2.33 (s, 6H), 2.08-1.97 (m, 2H), 1.11 (s, 3H), 0.70 (s, 3H).

Example 38

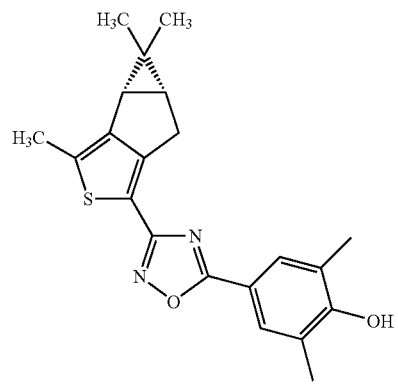

a) To a solution of 3,5-dimethyl-4-hydroxy benzoic acid (158 mg, 0.95 mmol), TBTU (305 mg, 0.95 mmol), DIPEA (0.49 mL, 2.85 mmol) in DMF (2.5 mL) is added (1aS,5aR)-N-hydroxy-1,1,2-trimethyl-1,1a,5,5a-tetrahydro-3-thia-cyclopropa[a]pentalene-4-carboxamidine (200 mg, 0.852 mmol) in DMF (3.5 mL). The resulting suspension is stirred at rt for 2 h. Another portion of 3,5-dimethyl-4-hydroxy benzoic acid (158 mg, 0.95 mmol), TBTU (305 mg, 0.95 mmol) and DIPEA (0.49 mL, 2.85 mmol) is added and stirring is continued for further 30 min. The reaction mixture is directly purified by prep. HPLC (Phenomenex Aqua 30×75 mm, 20 to 95% acetonitrile in water containing 0.5% formic acid) to give the hydroxyamidine ester intermediate (150 mg) as a colourless solid; LC-MS: $t_R$=1.04 min, $[M+1]^+$=385.20.

b) A solution of the above hydroxyamidine ester (150 mg, 0.40 mmol) in toluene is stirred at 110° C. for 35 h. The solvent is removed under reduced pressure and the residue is purified by prep. HPLC (Phenomenex Aqua 30×75 mm, 20 to 95% acetonitrile in water containing 0.5% formic acid) to give 2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenol (125 mg) as colourless solid; LC-MS: $t_R$=1.19 min, $[M+1]^+$=367.18; $^1$H NMR (CDCl$_3$): δ 7.80

(s, 2H), 5.07 (s, 1H), 3.06 (dd, J=5.9, 18.8 Hz, 1H), 2.89 (d, J=18.8 Hz, 1H), 2.42 (s, 3H), 2.33 (s, 6H), 1.98-1.90 (m, 2H), 1.15 (s, 3H), 0.78 (s, 3H).

Examples 39 to 43

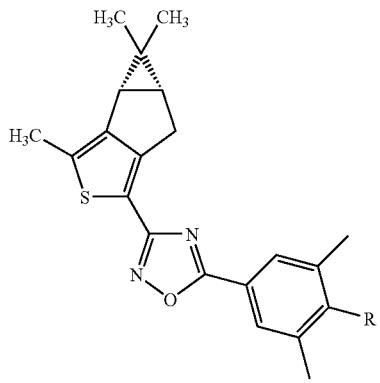

To a solution of (((1aS,5aR)-1,1,2-trimethyl-1,1a,5,5a-tetrahydro-3-thia-cyclopropa[a]pentalen-4-yl)-[1,2,4]oxadiazol-5-yl]-phenol (10 mg, 0.027 mmol) in isopropanol (1 mL) the corresponding alkylating agent (as bromide, chloride or mesylate) (0.135 mmol) and 2 N aq. NaOH (0.2 mL) are added. The reaction mixture is shaken for 10 h at 65° C. The reaction mixtures are purified by prep. HPLC (Waters XTerra Prep MS C18 19×50 mm 5 um, 80% to 5% water (0.85% NEt$_2$)/Acetonitrile) to give the desired products as colourless lyophilisates.

In the case of Example 43, the reaction mixture is shaken for 10 h at 80° C. To effect deprotection of the diol moiety, the product obtained after purification is dissolved in 1 mL CH$_3$COOH/H$_2$O 8:2 and allowed to stand for 2 h at rt before it is purified by prep. HPLC once more.

| Example | R | Scale (mmol) | LC-MS $t_R$ (min) | [M + H]$^+$ |
|---|---|---|---|---|
| 39 | ~O~~OH | 0.027 | 1.17 | 411.18 |
| 40 | ~O~~OH (with methyl) | 0.027 | 1.20 | 425.17 |
| 41 | ~O~~OH with OH | 0.027 | 1.10 | 441.23 |
| 42 | ~O~~OH with OH | 0.027 | 1.10 | 441.27 |
| 43 | ~O~~OH with OH | 0.027 | 1.12 | 455.29 |

Example 44

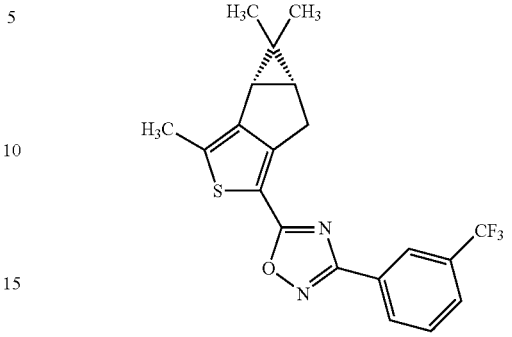

a) To an ice-cold suspension of K-tert-butylate (22.44 g, 200 mmol) and hydroxylamine hydrochloride (8.34 g, 120 mmol) in methanol (250 mL) 3-trifluoromethylbenzonitrile (6.84 g, 40 mmol) is added. The mixture is refluxed for 2.5 h, the solvent is removed under reduced pressure and the residue is dissolved in water. The solution is extracted twice with EA. The organic extracts are dried over Na$_2$SO$_4$, evaporated and dried under high vacuum to give N-hydroxy-3-trifluoromethyl-benzamidine (8.1 g) as a white solid, LC-MS: $t_R$=0.54 min, [M+1]$^+$=205.18.

b) To a solution of (1aS,5aR)-1,1,2-trimethyl-1,1a,5,5a-tetrahydro-3-thia-cyclopropa[a]pentalene-4-carboxylic acid (450 mg, 2.03 mmol), TBTU (715 mg, 2.23 mmol) and DIPEA (863 mg, 6.68 mmol) in DMF (7 mL) N-hydroxy-3-trifluoromethyl-benzamidine (455 mg, 2.23 mmol) is added and the mixture is stirred at rt for 1.5 h. Formic acid (1.2 mL) is added and the mixture is purified by prep. HPLC (Grom-Sil 120 ODS-4-HE, 30×75 mm, 10 μm, 20 to 95% acetonitrile in water containing 0.5% formic acid) to give (1aS,5aR)-1,1,2-trimethyl-1,1a,5,5a-tetrahydro-3-thia-cyclopropa[a]pentalene-4-carboxylic acid N-(N-hydroxy-3-trifluoromethylbenzamidine) ester (520 mg) as a colourless lyophilisate; LC-MS: $t_R$=1.12 min, [M+1]$^+$=409.20.

c) A solution of (1aS,5aR)-1,1,2-trimethyl-1,1a,5,5a-tetrahydro-3-thia-cyclopropa[a]pentalene-4-carboxylic acid N-(N-hydroxy-3-trifluoromethylbenzamidine) ester (480 mg) in toluene is refluxed for 7 days before the solvent is removed under reduced pressure. The residue is purified by CC on silica gel eluting with DCM to give 3-(3-trifluoromethyl-phenyl)-5-((1aS,5aR)-1,1,2-trimethyl-1,1a,5,5a-tetrahydro-3-thia-cyclopropa[a]pentalen-4-yl)-[1,2,4]oxadiazole (360 mg) as a pale yellow solid; LC-MS: $t_R$=1.26 min, [M+1]$^+$=391.2; $^1$H NMR (CDCl$_3$): δ 8.39 (s, 1H), 8.30 (d, J=7.6 Hz, 1H), 7.76 (d, J=8.2 Hz, 1H), 7.61 (t, J=7.6 Hz, 1H), 3.12 (dd, J=6.4, 18.8 Hz, 1H), 2.95 (d, J=18.8 Hz, 1H), 2.45 (s, 3H), 2.02-1.93 (m, 2H), 1.15 (s, 3H), 0.77 (s, 3H).

Example 45

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 μM GDP (Sigma, G-7127), 2.5% DMSO (Fluka, 41644), 50 μM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at room temperature. The assay is terminated by transfer of the reaction mixture to a Multiscreen plate (Millipore, MAHFC1H60) using a cell harvester from Packard Biosciences, and the plates are washed with ice-cold 10 mM $Na_2HPO_4/NaH_2PO_4$ (70%/30%), dried, sealed at the bottom and, after addition of 25 μl MicroScint20 (Packard Biosciences, order# 6013621), sealed on the top. Membrane-bound $^{35}$S-GTPγS is measured with a TopCount from Packard Biosciences.

$EC_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

Table 1 shows the $EC_{50}$ value of some Examples determined as described above:

TABLE 1

| Compound of Example | $EC_{50}$ [nM] |
|---|---|
| 6 | 12 |
| 16 | 0.9 |
| 19 | 1.2 |
| 24 | 4.8 |
| 27 | 6.1 |
| 32 | 8.8 |
| 38 | 1.6 |
| 39 | 1.1 |
| 43 | 1.4 |

Example 46

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean ±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 2 shows the effect on lymphocyte counts 6 h after oral administration of 10 mg/kg of two compounds of the present invention to normotensive male Wistar rats as compared to a group of animals treated with vehicle only.

TABLE 2

| Compound of Example | Lymphocyte counts |
|---|---|
| 16 | −49% |
| 19 | −56% |

The invention claimed is:

1. A compound of the Formula (I),

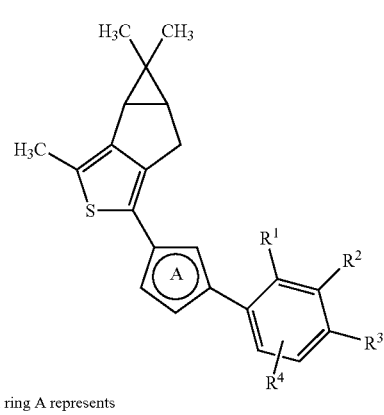

Formula (I)

wherein ring A represents

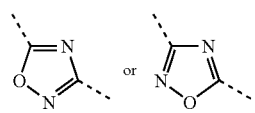

$R^1$ represents hydrogen, lower alkyl, lower alkoxy, or halogen;

$R^2$ represents hydrogen, lower alkyl, lower alkoxy, trifluoromethyl, trifluoromethoxy, or halogen;

$R^3$ represents hydrogen, hydroxy-lower alkyl, 2,3-dihydroxypropyl, di-(hydroxy-lower alkyl)-lower alkyl, —$CH_2$—$(CH_2)_k$—$NR^{31}R^{32}$, (azetidine-3-carboxylic acid)-1-yl-methyl, (azetidine-3-carboxylic acid lower alkylester)-1-yl-methyl, 2-[(azetidine-3-carboxylic acid)-1-yl]-ethyl, 2-[(azetidine-3-carboxylic acid lower alkylester)-1-yl]-ethyl, 3-[(azetidine-3-carboxylic acid)-1-yl]-propyl, 3-[(azetidine-3-carboxylic acid lower alkylester)-1-yl]-propyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, 2-[(pyrrolidine-3-carboxylic acid)-1-yl]-ethyl, 2-[(pyrrolidine-3-carboxylic acid lower alkylester)-1-yl]-ethyl, 2-[(pyrrolidine-2-carboxylic acid)-1-yl]-ethyl, 2-[(pyrrolidine-2-carboxylic acid lower alkylester)-1-yl]-ethyl, 3-[(pyrrolidine-3-carboxylic acid)-1-yl]-propyl, 3-[(pyrrolidine-3-carboxylic acid lower alkylester)-1-yl]-propyl, 3-[(pyrrolidine-2-carboxylic acid)-1-yl]-propyl, 3-[(pyrrolidine-2-carboxylic acid lower alkylester)-1-yl]-propyl, —$CH_2$—$(CH_2)_n$—$CONR^{31}R^{32}$, —CO—$NHR^{31}$, —$(CH_2)_n$CH(OH)—$CH_2$—$NR^{31}R^{32}$, hydroxy, lower alkoxy, fluoro-lower alkoxy, hydroxy-lower alkoxy, di-(hydroxy-lower alkyl)-lower alkoxy, 1-glyceryl, 2-glyceryl, 2-hydroxy-3-methoxy-propoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-(lower alkyl)-piperazin-1-yl]- ethoxy, 2-[4-(2-hydroxy-ethyl)-piperazin-1-yl]-ethoxy, 3-piperazin-1-yl-propoxy, 3-[4-(lower alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 3-carbamoyl-propoxy, 3-(lower alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(lower alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_n$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$;

R$^{31}$ represents hydrogen, methyl, ethyl, 1-propyl, 2-propyl, 2-hydroxyethyl, 2-hydroxy-1-hydroxymethyl-ethyl, 2-lower alkoxyethyl, 3-hydroxypropyl, 3-lower alkoxypropyl, 2-aminoethyl, 2-(lower alkylamino)ethyl, 2-(di-(lower alkyl)amino)ethyl, carboxymethyl, lower alkylcarboxymethyl, 2-carboxyethyl, or 2-(lower alkylcarboxy)ethyl;

R$^{32}$ represents hydrogen, methyl, or ethyl;

R$^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

R$^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

n represents 0, 1, or 2; and

R$^4$ represents hydrogen, lower alkyl, or halogen, in free form or an optically pure enantiomer, a mixture of enantiomers, a diastereomer, a mixture of diastereomers, a diastereomeric racemate, or a mixture of diastereomeric racemates, or a salt, form of said compound.

2. The compound according to claim 1, wherein the compound is of the following formula:

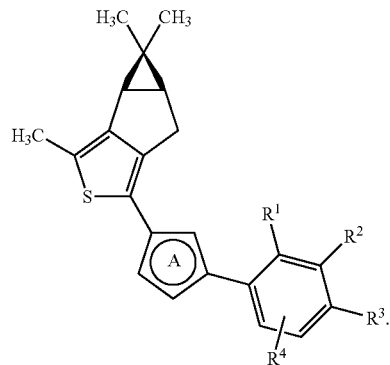

3. The compound according to claim 1, wherein the compound is of the following formula:

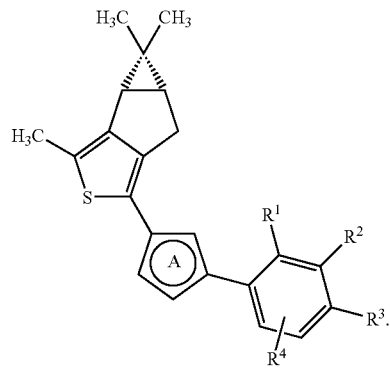

4. The compound according to claim 1, wherein the compounds is of the following formula:

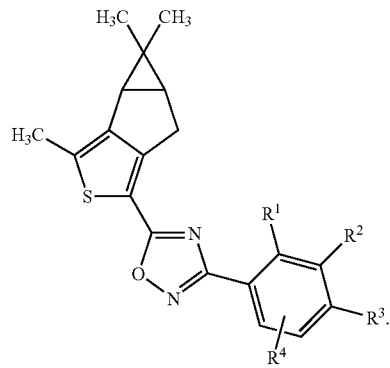

5. The compound according claim 1, wherein the compound is of the following formula:

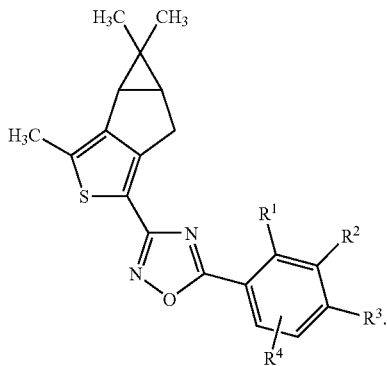

6. The compound according to claim 1, wherein $R^1$, $R^2$, and $R^4$ represent hydrogen.

7. The compound according to claim 1, wherein $R^1$ represents hydrogen and $R^2$ and $R^4$ represent a methyl group.

8. The compound according to claim 1, wherein $R^1$ represents hydrogen, $R^2$ represents a methyl group and $R^4$ represents an ethyl group.

9. The compound according to claim 1, wherein $R^1$ represents hydrogen, $R^2$ represents a methoxy group and $R^4$ represents chlorine.

10. The compound according to claim 1, wherein $R^3$ represents hydrogen, hydroxy-lower alkyl, 2,3-dihydroxypropyl, di-(hydroxy-lower alkyl)-lower alkyl, —CH$_2$—(CH$_2$)$_k$—NR$^{31}$R$^{32}$, (azetidine-3-carboxylic acid)-1-yl-methyl,(azetidine-3-carboxylic acid lower alkylester)-1-yl-methyl, 2-[(azetidine-3-carboxylic acid)-1-yl]-ethyl, 2-[(azetidine-3-carboxylic acid lower alkylester)-1-yl]-ethyl, 3-[(azetidine-3-carboxylic acid)-1-yl]-propyl, 3-[(azetidine-3-carboxylic acid lower alkylester)-1-yl]-propyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, 2-[(pyrrolidine-3-carboxylic acid)-1-yl]-ethyl, 2-[(pyrrolidine-3-carboxylic acid lower alkylester)-1-yl]-ethyl, 2-[(pyrrolidine-2-carboxylic acid)-1-yl]-ethyl, 2-[(pyrrolidine-2-carboxylic acid lower alkylester)-1-yl]-ethyl, 3-[(pyrrolidine-3-carboxylic acid)-1-yl]-propyl, 3-[(pyrrolidine-3-carboxylic acid lower alkylester)-1-yl]-propyl, 3-[(pyrrolidine-2-carboxylic acid)-1-yl]-propyl, 3-[(pyrrolidine-2-carboxylic acid lower alkylester)-1-yl]-propyl, —CH$_2$—(CH$_2$)$_n$—CONR$^{31}$R$^{32}$, —CO—NHR$^{31}$, —(CH$_2$)$_n$CH(OH)—CH$_2$—NR$^{31}$R$^{32}$, hydroxy, lower alkoxy, fluoro-lower alkoxy, hydroxy-lower alkoxy, di-(hydroxy-lower alkyl)-lower alkoxy, 1-glyceryl, 2-glyceryl, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(lower alkyl)-piperazin-1-yl]-ethoxy, 2-[4-(2-hydroxy-ethyl)-piperazin-1-yl]-ethoxy, 3-piperazin-1-yl-propoxy, 3-[4-(lower alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 3-carbamoyl-propoxy, 3-(lower alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(lower alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, or —NR$^{31}$R$^{32}$, —NHCO—R$^{31}$ and wherein R$^{31}$ and R$^{32}$ are as defined in claim 1.

11. The compound according to claim 1, wherein $R^3$ represents hydroxy-lower alkoxy, di-(hydroxy-lower alkyl)-lower alkoxy, 1-glyceryl, 2-glyceryl, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(lower alkyl)-piperazin-1-yl]-ethoxy, 2-[4-(2-hydroxy-ethyl)-piperazin-1-yl]-ethoxy, 3-piperazin-1-yl-propoxy, 3-[4-(lower alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 3-carbamoyl-propoxy, 3-(lower alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(lower alkyl)-piperazin-1-yl]-propoxy, 2-hydroxy-3-[4-(2-hydroxy-ethyl)-piperazin-1-yl]-propoxy, or 2-hydroxy-3-morpholin-4-yl-propoxy and wherein R$^{31}$ and R$^{32}$ are as defined in claim 1.

12. The compound according to claim 1, wherein $R^3$ represents hydroxy-lower alkyl, 2,3-dihydroxypropyl, di-(hydroxy-lower alkyl)-lower alkyl, —$CH_2$—$(CH_2)_k$—$NR^{31}R^{32}$, (azetidine-3-carboxylic acid)-1-yl-methyl, (azetidine-3-carboxylic acid lower alkylester)-1-yl-methyl, 2-[(azetidine-3-carboxylic acid)-1-yl]-ethyl, 2-[(azetidine-3-carboxylic acid lower alkylester)-1-yl]-ethyl, 3-[(azetidine-3-carboxylic acid)-1-yl]-propyl, 3-[(azetidine-3-carboxylic acid lower alkylester)-1-yl]-propyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, 2-[(pyrrolidine-3-carboxylic acid)-1-yl]-ethyl, 2-[(pyrrolidine-3-carboxylic acid lower alkylester)-1-yl]-ethyl, 2-[(pyrrolidine-2-carboxylic acid)-1-yl]-ethyl, 2-[(pyrrolidine-2-carboxylic acid lower alkylester)-1-yl]-ethyl, 3-[(pyrrolidine-3-carboxylic acid)-1-yl]-propyl, 3-[(pyrrolidine-3-carboxylic acid lower alkylester)-1-yl]-propyl, 3-[(pyrrolidine-2-carboxylic acid)-1-yl]-propyl, 3-[(pyrrolidine-2-carboxylic acid lower alkylester)-1-yl]-propyl, —$CH_2$—$(CH_2)_n$—$CONR^{31}R^{32}$, —CO—$NHR^{31}$, or —$(CH_2)_n CH(OH)$—$CH_2$—$NR^{31}R^{32}$ and wherein $R^{31}$ and $R^{32}$ are as defined in claim 1.

13. The compound according to any claim 1, wherein $R^3$ represents di-(hydroxy-lower alkyl)-lower alkoxy, 1-glyceryl, —$OCH_2$—$(CH_2)_m$—$NR^{31}R^{32}$, —O—$CH_2$—$CONR^{31}R^{32}$, or —$OCH_2$—CH(OH)—$CH_2$—$NR^{31}R^{32}$, wherein $R^{31}$ represents methyl or 2-hydroxyethyl and $R^{32}$ represents hydrogen.

14. The compound according to claim 1, wherein $R^3$ represents —$CH_2$—$(CH_2)_k$—$NHSO_2R^{33}$, —$(CH_2)_n CH(OH)$—$CH_2$—$NHSO_2R^{33}$, —$OCH_2$—$(CH_2)_m$—$NHSO_2R^{33}$, —$OCH_2$—CH(OH)—$CH_2$—$NHSO_2R^{33}$, —$CH_2$—$(CH_2)_k$—$NHCOR^{34}$, —$(CH_2)_n CH(OH)$—$CH_2$—$NHCOR^{34}$— $OCH_2$—$(CH_2)_m$—$NHCOR^{34}$ or —$OCH_2$—CH(OH)—$CH_2$—$NHCOR^{34}$ and wherein $R^{33}$ and $R^{34}$ are as defined in claim 1.

15. The compound according to claim 1 selected from the group consisting of:

- 4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol;
- 2-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethanol;
- 1-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-2-ol;
- (2S)-3-{4-[5-((1aS,5aR)-1,1,2-trimethyl-1,1a, 5,5a-tetrahydro-3-thia-cyclopropa[a]pentalen-4-yl)-[1,2,4]oxadiazol-3-yl]-phenoxy}-propane-1,2-diol;
- (2R)-3-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propane-1,2-diol;
- 1-methoxy-3-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-2-ol;
- 2-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-propane-1,3-diol;
- 3-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-1-ol;
- dimethyl-(2-{4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethyl)-amine;
- 2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenol;
- 2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethanol;
- 1-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-2ol;
- (2S)-3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propane-1,2-diol;
- (2R)-3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propane-1,2-diol;
- 1-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-3-methoxy-propan-2-ol;
- 2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-propane-1,3-diol;
- 3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propan-1-ol;
- (2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethyl)-dimethyl-amine;
- 3-[3,5-dimethyl-4-(2-pyrrolidin-1-yl-ethoxy)-phenyl]-5-((1aS,5aR)-1,1,2-trimethyl-1,1a,5,5a-tetrahydro-3-thia-cyclopropa[a]pentalen-4-yl)-[1,2,4]oxadiazole;
- 4-(2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-ethyl)-morpholine;
- 3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propylamine;
- (3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-methyl-amine;
- (3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-dimethyl-amine;
- 2-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propylamino)-ethanol;
- 3-[3,5-dimethyl-4-(3-pyrrolidin-1-yl-propoxy)-phenyl]-5-((1aS,5aR)-1,1,2-trimethyl-1,1a,5,5a-tetrahydro-3-thia-cyclopropa[a]pentalen-4-yl)-[1,2,4]oxadiazole;
- (3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-propyl-amine;
- 2-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propylamino)-propane-1,3-diol;
- $N_1$-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-ethane-1,2-diamine,
- 1-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-pyrrolidine-2-carboxylic acid;

1-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-pyrrolidine-3-carboxylic acid;

2-[4-(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-piperazin-1-yl]-ethanol;

2-amino-2-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxymethyl}-propane-1,3-diol;

(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-isopropyl-amine;

(3-{2,6-dimethyl-4-[5-((1aS,5aR)-1,1,2-trimethyl-1,1a,5,5a-tetrahydro-3-thia-cyclopropa[a]pentalen-4-yl)-[1,2,4]oxadiazol-3-yl]-phenoxy}-propyl)-(2-ethoxy-ethyl)-amine;

2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenol;

2-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxy}-ethanol;

1-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxy}-propan-2-ol;

3-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxy}-propane-1,2-diol;

3-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxy}-propane-1,2-diol;

2-{2,6-dimethyl-4-[3-((1aS,5aR)-1,1,2-trimethyl-1,1a,5,5a-tetrahydro-3-thia-cyclopropa[a]pentalen-4-yl)-[1,2,4]oxadiazol-5-yl]-phenoxymethyl}-propane-1,3-diol; and 3-(3-trifluoromethyl-phenyl)-5-((1aS,5aR)-1,1,2-trimethyl-1,1a,5,5a-tetrahydro-3-thia-cyclopropa[a]pentalen-4-yl)-[1,2,4]oxadiazole.

16. A pharmaceutical composition comprising the compound according to claim 1 and a pharmaceutically acceptable carrier.

17. A method for preparing a pharmaceutical composition, comprising mixing one or more compound(s) of claim 1 with an inert excipient.

* * * * *